(12) United States Patent
Garfield et al.

(10) Patent No.: US 10,555,955 B2
(45) Date of Patent: Feb. 11, 2020

(54) TRIMEGESTONE (TMG) FOR TREATMENT OF PRETERM BIRTH

(71) Applicant: DIGNITY HEALTH, Phoenix, AZ (US)

(72) Inventors: Robert E. Garfield, Goodyear, AZ (US); Shao-Qing Shi, Goodyear, AZ (US); Leili Shi, Goodyear, AZ (US)

(73) Assignee: Dignity Health, Phoenix, AZ (US)

( * ) Notice: Subject to any disclaimer, the term of this patent is extended or adjusted under 35 U.S.C. 154(b) by 56 days.

(21) Appl. No.: 15/706,444

(22) Filed: Sep. 15, 2017

(65) Prior Publication Data
US 2018/0000838 A1 Jan. 4, 2018

Related U.S. Application Data

(60) Continuation of application No. 15/004,676, filed on Jan. 22, 2016, now abandoned, which is a division of
(Continued)

(51) Int. Cl.
*A61K 31/575* (2006.01)
*A61K 9/00* (2006.01)
(Continued)

(52) U.S. Cl.
CPC .......... *A61K 31/575* (2013.01); *A61K 9/0014* (2013.01); *A61K 9/0053* (2013.01);
(Continued)

(58) Field of Classification Search
None
See application file for complete search history.

(56) References Cited

U.S. PATENT DOCUMENTS 5,370,135 A * 12/1994 Dullien ................ G01N 33/743
128/898
2004/0110732 A1  6/2004 Masini-Efeve et al.
(Continued)

FOREIGN PATENT DOCUMENTS

CA         2677354 A1     8/2008
WO   WO-2008096122 A2 *  8/2008  ............. A61K 31/57

OTHER PUBLICATIONS

Kuon et al., "Pharmacological actions of progestins to inhibit cervical ripening and prevent delivery depend on their properties, the route of administration, and the vehicle", American Journal of Obstetrics and Gynecology, 202 (5):455e1-455e9 (May 2010).

*Primary Examiner* — Bethany P Barham
*Assistant Examiner* — Barbara S Frazier
(74) *Attorney, Agent, or Firm* — Rodney J. Fuller; Booth Udall Fuller, PLC

(57) ABSTRACT

As disclosed herein, novel compositions including steroid hormones, such as trimegestone (TMG) and progesterone (P4), provide treatments for term and preterm labor with significant effects on the delay of delivery. Delay and block of delivery occurs when both P4 and TMG are administered late in gestation in pregnant rat and guinea pig animal models. TMG exhibits remarkable drug efficacy, achieving the same inhibition as P4, but at much lower doses. These hereto unknown effects of TMG on the processes of cervical ripening and uterine contraction provide a novel approach for extending pregnancy term, including reducing a likelihood of preterm and/or term labor, along with improved methods of administration. Other diseases and/or conditions may be treated with TMG, such as dysmenorrhea or luteal insufficiency for sustaining pregnancy.

14 Claims, 11 Drawing Sheets

Related U.S. Application Data application No. 13/880,031, filed as application No. PCT/US2011/058141 on Oct. 27, 2011, now Pat. No. 9,271,991.

(60) Provisional application No. 61/434,309, filed on Jan. 19, 2011, provisional application No. 61/407,388, filed on Oct. 27, 2010.

(51) Int. Cl.
<table>
<tr><td>A61K 31/4418</td><td>(2006.01)</td></tr>
<tr><td>A61K 31/405</td><td>(2006.01)</td></tr>
<tr><td>A61K 31/4422</td><td>(2006.01)</td></tr>
<tr><td>A61K 33/06</td><td>(2006.01)</td></tr>
<tr><td>A61K 45/06</td><td>(2006.01)</td></tr>
<tr><td>A61K 47/44</td><td>(2017.01)</td></tr>
<tr><td>A61K 38/095</td><td>(2019.01)</td></tr>
</table>

(52) U.S. Cl.
CPC ........ *A61K 31/405* (2013.01); *A61K 31/4418* (2013.01); *A61K 31/4422* (2013.01); *A61K 33/06* (2013.01); *A61K 45/06* (2013.01); *A61K 47/44* (2013.01); *A61K 9/0019* (2013.01); *A61K 38/095* (2019.01)

(56) References Cited

U.S. PATENT DOCUMENTS

2005/0020552 A1* 1/2005 Aschkenasy ......... A61K 9/0014
    514/177
2006/0024725 A1  2/2006 Hussa et al.
2009/0093448 A1  4/2009 Pfaff et al.

* cited by examiner

Delivery Delay in Pregnant Rats Treated with s.c P4 or TMG with Different Doses Starting on D20 of Gestation

TRIMEGESTONE (TMG) FOR TREATMENT OF PRETERM BIRTH

This application claims priority to U.S. Ser. No. 61/407,388 filed Oct. 27, 2010 and to U.S. Ser. No. 61/434,309 filed Jan. 19, 2011, the contents of all of which are herein incorporated by reference.

FIELD OF THE INVENTION

The present invention relates to methods and compositions related to obstetrics and gynecological diseases and/or conditions.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Preterm birth (less than 37 completed weeks of gestation) is one of the major problems and challenges in obstetrics. The frequency of preterm births is about 12-13% in the USA and 5-9% in many other developed countries.[1,2] Despite all efforts to reduce the number of preterm births the problem is continuing to escalate. Since 1990 the percentage of births delivered preterm has risen more than 20 percent and is 36 percent higher since the early 1980s in the USA.[3] Preterm birth is not only a major determinant of neonatal and infant morbidity, including neurodevelopmental handicaps, chronic respiratory problems, intraventricular hemorrhage, infection, retrolental fibroplasia, and necrotizing enterocolitis, but it is also the single most important cause of perinatal mortality in North America, Europe and particularly in undeveloped countries.[4] Additionally, the neonatal and long-term health care costs of preterm infants impose a considerable economic strain both on individual families and on healthcare costs (>$26.2 billion in 2005 in the USA).[5,53] There is a need in the art for novel and effective treatments for preterm delivery.

Both uterine and cervical functions play important roles in the onset and progression of term and preterm labor and delivery. Ripening of the cervix is an inflammatory-like reaction with infiltration of leukocytes, increase of cytokines (interleukin (IL)-1 and IL-8) and an increase in metallopro-teinases (MMPs), with MMPs playing a key role in ECM remodeling.[8,9,10] Following cervical ripening, uterine contraction and cervical dilation results in delivery of the fetus. Uterine contraction results from the biomechanical coupling of actin and myosin, which depends on the phosphorylation of myosin by myosin light-chain kinase (MLCK). The activation of MLCK by various uterotonins, including oxytocin and prostaglandins, fosters actin-myosin coupling, leading to synchronous high-amplitude activity in cell-cell connections that generate contractions in the uterus.

Both processes of cervical ripening and uterine contractility are regulated by steroid hormones (in particular progesterone (P4) and estrogen) and progesterone has been known to be used for recurrent or high risk preterm labor (PTL).[17-26,32] However, P4 used to treat preterm labor and uterine contractile disorders is often delivered through inconvenient and less effective routes of vaginal, oral or intramuscular delivery. Further, P4 exhibits some measure of non-specificity for non-progesterone receptors, leading to potentially undesirable side effects.

Trimegestone (TMG), a 19-norpregnane derivative progestin, has been used in clinical trials as a proposed treatment for hormone replacement therapy, as well as for oral contraception.[57-62] To date, the efficacy of compounds such as TMG has not been shown in treatments for pre-term pregnancy. As a "next generation" progestin (i.e., synthetic or exogenous progestogen), TMG exhibits a 6-fold higher affinity for progesterone receptor (PR) than P4, with much greater potency.[11,12] This activity is coupled with higher selectivity for the PR compared to other steroid hormone receptors. For example, TMG binds with low affinity to the androgen, glucocorticoid and mineralocorticoid receptor and has no measurable affinity for the estrogen receptor.[12,14,64,65] These pharmacological differences may result in notably different biological effects. For example, TMG also exhibits a differential effect on MMP expression in cultured stromal cells when compared to P4 administration.[13] TMG also exhibits antiestrogenic activity in processes related to rat uterine decidualization and ovulation assays, and possesses the highest level of estrogenic activity antagonism in the uterine endometrium among reference progestins.[67] Together, these results suggest TMG may be a potent compound for inhibiting cervical ripening and uterine contractility, with further opportunities to apply TMG in new therapeutic avenues, such as dysmenorrhea.[68]

These features of TMG present intriguing questions of how TMG application for preterm pregnancy treatment compares to P4 administration, and if higher PR specificity coupled with different mechanisms of action may lead to improved methods of treatment and/or administration.[11]

SUMMARY OF THE INVENTION

The following embodiments and aspects thereof are described and illustrated in conjunction with compositions and methods which are meant to be exemplary and illustrative, not limiting in scope. In one embodiment, the invention includes a method of extending pregnancy term in a subject in need thereof, including providing a quantity of a composition comprising a 19-norprogesterone, or a pharmaceutical equivalent, derivative, analog, and/or salt thereof, and administering the quantity of the composition to the subject in need thereof. In another embodiment, the 19-norprogesterone is a compound of the formula:

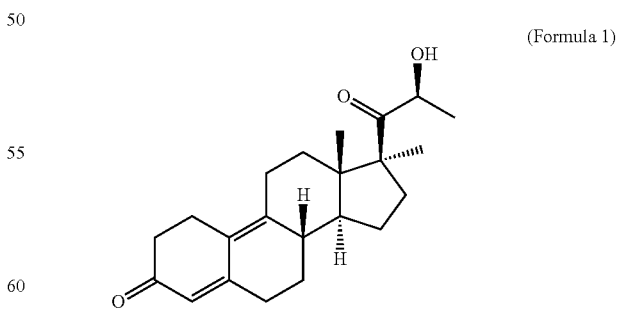

(Formula 1)

or a pharmaceutical equivalent, derivative, analog, and/or salt thereof. In another embodiment, the composition further includes one or more solubilizing factors. In one embodiment, the one or more solubilizing factors is selected from the group of: cyclodextrins, sesame oil, fish oil, corn oil, olive oil, coconut oil, krill oil, omega fatty acids, mineral oil, peppermint oil, flaxseed oil, vitamin E oil, argan oil, saline solution and glucose solution. In another embodiment, the composition is administered through nasal, oral, subcutaneous, transmucosal, transdermal, parenteral, implantable pump, continuous infusion, topical, intradermal, intravenous, intramuscular, intraperitoneal, inhalation, rectal, non-vaginal and/or vaginal delivery. In one embodiment, the method further includes administering of one or more compounds selected from the group consisting of: nifedipine, indomethacin, magnesium sulfate, oxytocin antagonists, and tocolytics. In another embodiment, the one or more compounds is administered after administering the quantity of the composition comprising a 19-norprogesterone, or a pharmaceutical equivalent, derivative, analog, and/or salt thereof. In another embodiment, the composition is administered at least twice daily. In another embodiment, the composition is administered to the subject in the range of: 0.01-0.1 mg, 0.1-0.5 mg 0.5-1 mg, 1-5 mg, 5-10 mg, 10-15 mg, 15-20 mg, and/or 20-100 mg. In one embodiment, the pregnancy term is at least 22 weeks. In one embodiment, the pregnancy term is at least 37 weeks.

Another embodiment of the present invention provides a pharmaceutical composition, including a therapeutically effective amount of a 19-norprogesterone, or a pharmaceutical equivalent, derivative, analog, and/or salt thereof, and a pharmaceutically acceptable carrier. In one embodiment, the 19-norprogesterone is a compound of the formula:

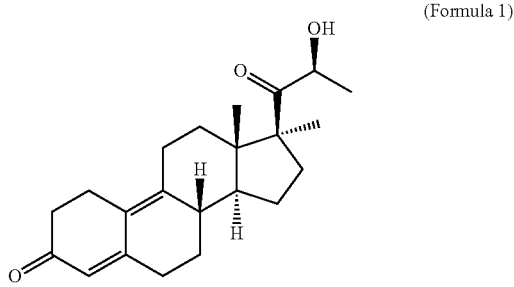

(Formula 1)

or a pharmaceutical equivalent, derivative, analog, and/or salt thereof. In another embodiment, the composition further includes one or more solubilizing factors. In another embodiment, the one or more solubilizing factors is selected from the group of: cyclodextrins, sesame oil, fish oil, corn oil, olive oil, coconut oil, krill oil, omega fatty acids, mineral oil, peppermint oil, flaxseed oil, vitamin E oil, argan oil, saline solution and glucose solution. In another embodiment, the pharmaceutical composition further includes one or more compounds selected from the group consisting of: nifedipine, indomethacin, magnesium sulfate, oxytocin antagonists, and tocolytics. In another embodiment, the pharmaceutical composition is provided in a dosage in the range of: 0.01-0.1 mg, 0.1-0.5 mg 0.5-1 mg, 1-5 mg, 5-10 mg, 10-15 mg, 15-20 mg, and/or 20-100 mg.

Another embodiment of the present invention provides a method of treating a disease and/or condition in a subject in need thereof including providing a quantity of a composition comprising a 19-norprogesterone, or a pharmaceutical equivalent, derivative, analog, and/or salt thereof; and administering the quantity of the composition to the subject in need thereof.

In another embodiment, the 19-norprogesterone is a compound of the formula:

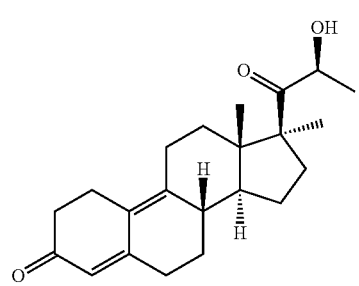

(Formula 1)

or a pharmaceutical equivalent, derivative, analog, and/or salt thereof. In another embodiment, the composition further includes one or more solubilizing factors. In another embodiment, the one or more solubilizing factors is selected from the group of: cyclodextrins, sesame oil, fish oil, corn oil, olive oil, coconut oil, krill oil, omega fatty acids, mineral oil, peppermint oil, flaxseed oil, vitamin E oil, argan oil, saline solution and glucose solution. In another embodiment, the composition is administered through nasal, oral, subcutaneous, transmucosal, transdermal, parenteral, implantable pump, continuous infusion, topical, intradermal, intravenous, intramuscular, intraperitoneal, inhalation, rectal, non-vaginal and/or vaginal delivery. In another embodiment, composition further includes administering one or more compounds selected from the group of: nifedipine, indomethacin, magnesium sulfate, oxytocin antagonists, and tocolytics. In another embodiment, the one or more compounds is administered after administering the quantity of the composition comprising a 19-norprogesterone, or a pharmaceutical equivalent, derivative, analog, and/or salt thereof. In another embodiment, the composition is administered twice daily. In another embodiment, composition is administered to the subject in the range of: 0.01-0.1 mg, 0.1-0.5 mg 0.5-1 mg, 1-5 mg, 5-10 mg, 10-15 mg, 15-20 mg, and/or 20-100 mg. In another embodiment, disease and/or condition is selected from the group of: preterm labor, term labor, luteal insufficiency, dysmenorrhea, dysfunctional uterine bleeding, and combinations thereof. In another embodiment, the disease and/or condition is dysmenorrhea. In another embodiment, the disease and/or condition is luteal insufficiency.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
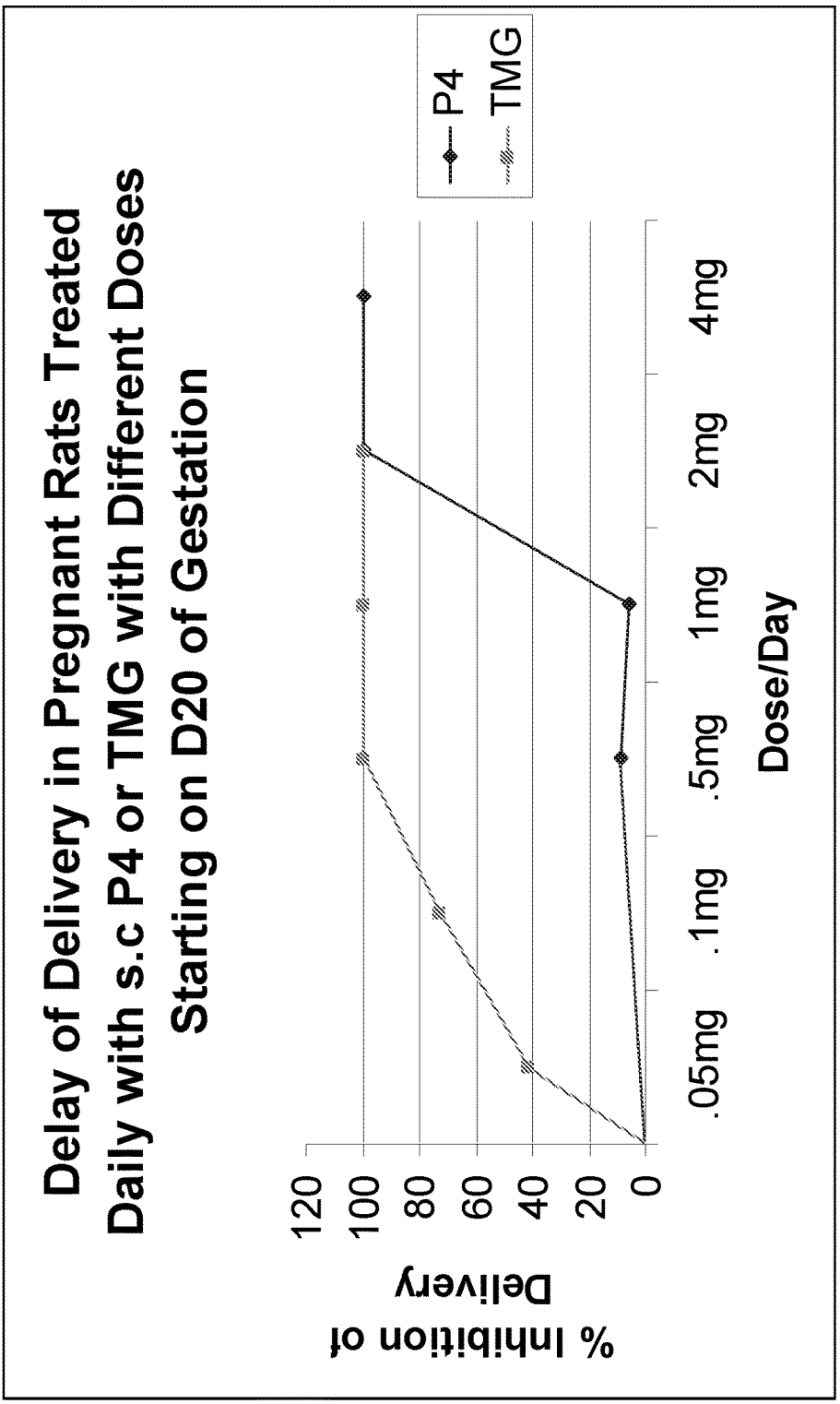
FIG. 1 depicts, in accordance with an embodiment herein, a graph comparing the effects of progesterone (P4) and trimegestone (TMG), administered subcutaneously (s.c.), on delay of delivery in pregnant rats. Note that in this and subsequent figures 100% delay indicates 80 hours beyond the normal delivery time on day 22 of gestation.
Figure 2:
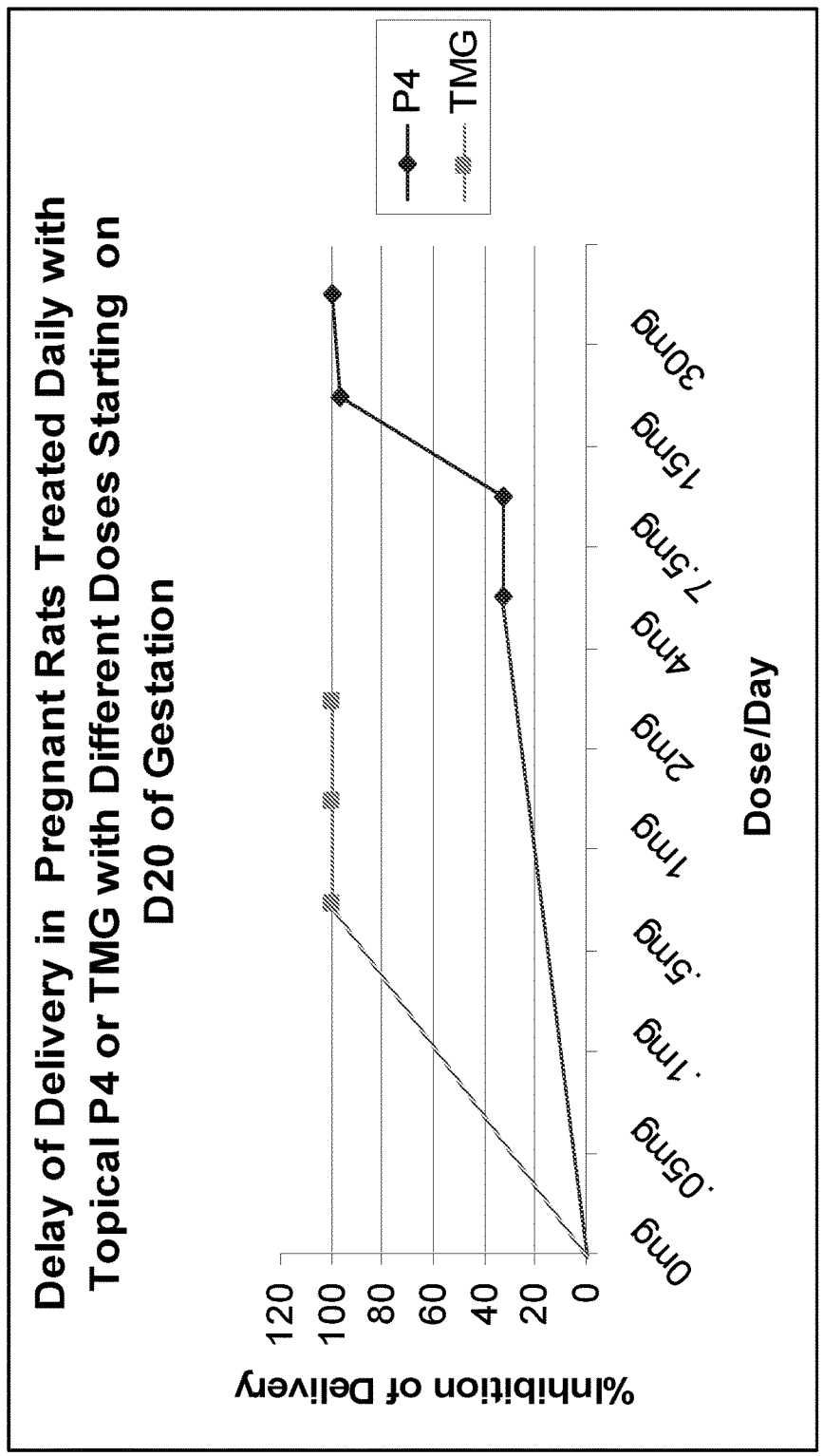
FIG. 2 depicts, in accordance with an embodiment herein, a graph comparing the effects of progesterone (P4) and trimegestone (TMG), administered topically, on delay of delivery on pregnant rats.
Figure 3:
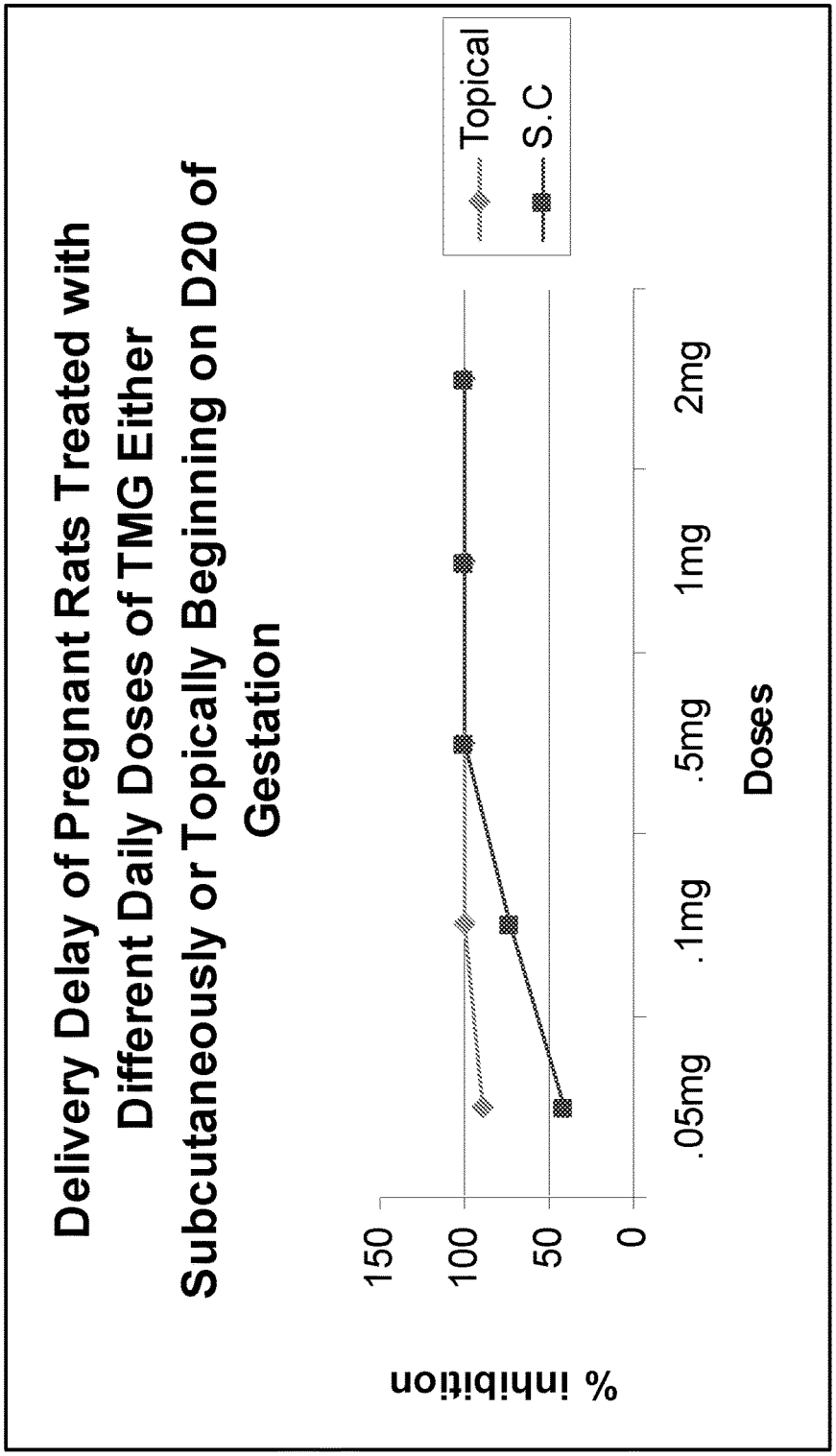
FIG. 3 depicts, in accordance with an embodiment herein, a graph comparing the effect on delay of delivery by different dosages of trimegestone (TMG), administered either topically or subcutaneously (s.c.) as indicated.
Figure 4:
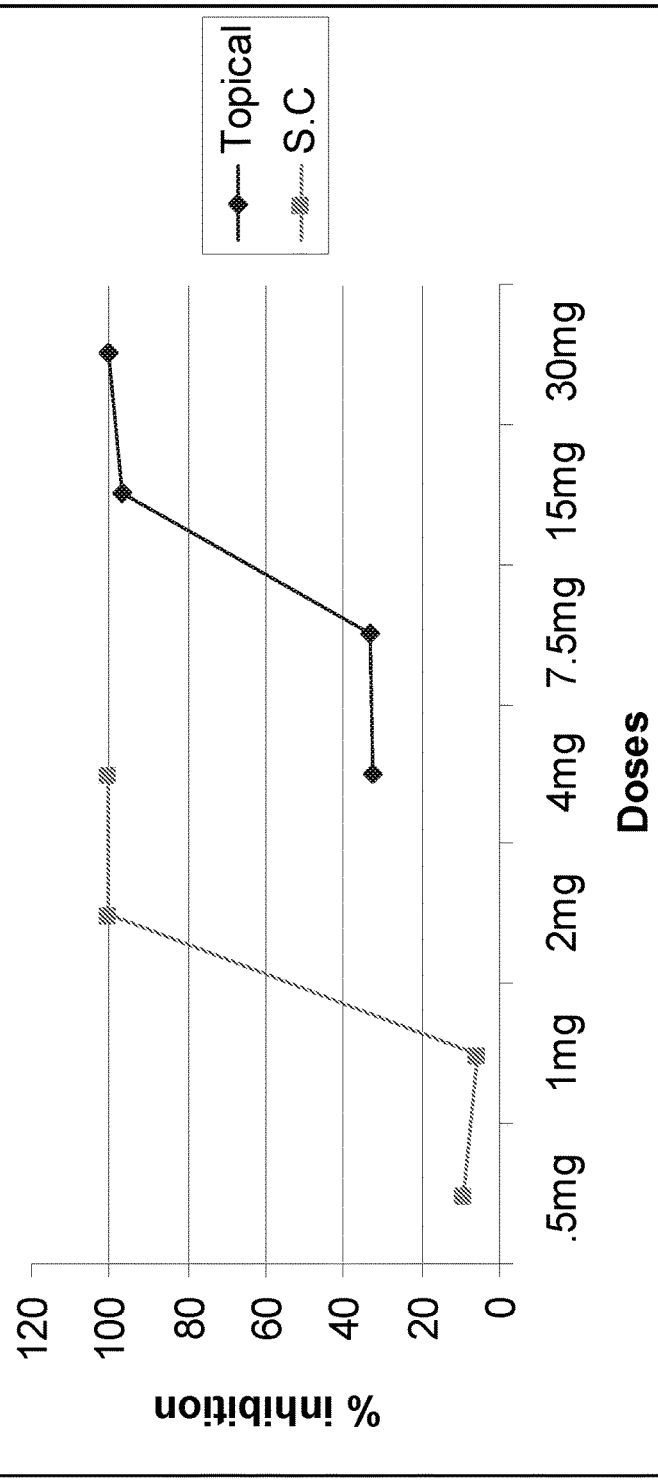
FIG. 4 depicts, in accordance with an embodiment herein, a graph comparing the effect on delay of delivery by different dosages of progesterone (P4), administered either topically or subcutaneously (s.c.) as indicated.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), and *Remington: The Science and Practice of Pharmacy* (Gennaro ed. 20th edition, Williams & Wilkins Pa., USA) (2000) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

As used herein, the abbreviation "TMG" means trimegestone (also known as RU-27987), or a compound of the formula:

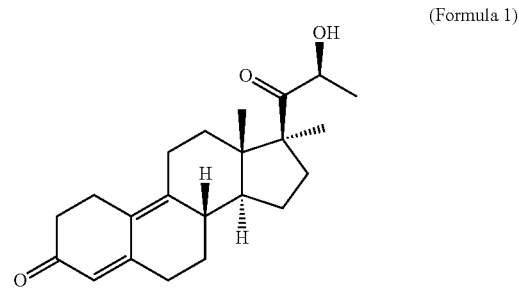

(Formula 1)

As used herein, the abbreviation "P4" means progesterone, or a compound of the formula:

(Formula 2)

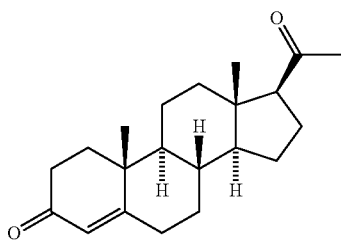

As used herein, promegestone (also known as R5020) has the formula:

(Formula 3)

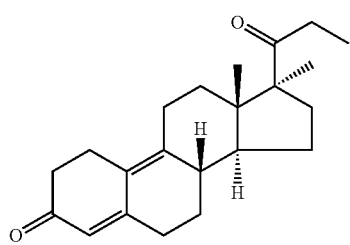

As used herein, nomegestrol has the formula:

(Formula 4)

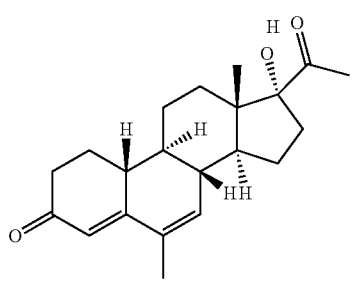

As used herein, nomegestrol acetate has the formula:

(Formula 5)

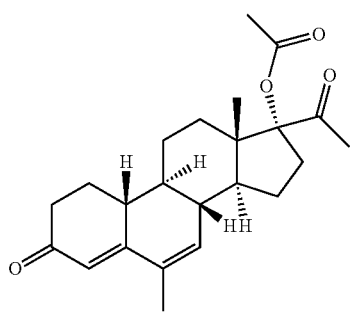

As used herein, demegestone has the formula:

(Formula 6)

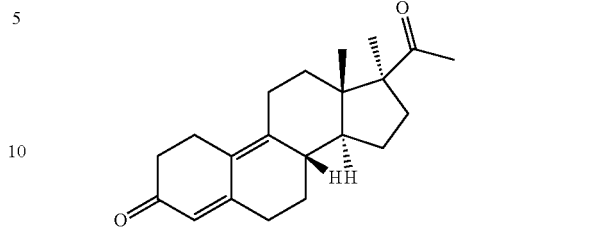

As used herein, nestorone has the formula:

(Formula 7)

As used herein, nomegestrol has the formula:

Labor is a multifactorial process involving several different pathways converging together to result in the birth of an animal. During most of the pregnancy term, the cervix forms a firm, rigid closed state protecting the fetus from the environment, while the uterus remains relatively quiescent. An activation phase involving uterine stretch is followed by a stimulation phase with a progressive cascade of events involving cervical ripening, uterine contractility, decidual and fetal membrane activation.

A key step in this cascade of events, cervical ripening, is an active biochemical process occurring independently of the processes underlying uterine contractility. The cervix is dominated by fibrous connective tissue that is composed of an extracellular matrix which consists mostly of collagen (70% type I and ~30% type III[6]) with elastin and proteoglycans and a cellular portion that consists of smooth muscles, fibroblasts, epithelium and blood vessels. Studies have shown that the process of cervical ripening is associated with a strong reorganization of the extracellular matrix (ECM), especially collagen. Not only does the concentration decrease by 30-70%, but there is also a switch from insoluble to more soluble collagen.[6,7] Ripening of the cervix is an inflammatory-like reaction with infiltration of leukocytes, increase of cytokines (interleukin (IL)-1 and IL-8) and an increase in metalloproteinases (MMPs), with MMPs playing a key role in ECM remodeling.[8,9,10]

Cervical ripening, followed by uterine contraction and dilation of the cervix, ultimately results in the delivery of the fetus. Uterine contraction results from the coupling of actin and myosin, which depends on the phosphorylation of myosin by myosin light-chain kinase (MLCK). MLCK is activated by various uterotonins, including oxytocin and prostaglandins. Actin-myosin couplings, operating through cell-to-cell connections, generate the biomechanical signal leading to synchronous high-amplitude uterine contractions during labor.

These distinct processes of cervical ripening and uterine contractility are at least partially regulated by steroid hormones (in particular, progesterone (P4) and estrogen). For example, progesterone has been as an effective treatment for recurrent or high risk preterm labor (PTL).[17-26,12] However, steroid hormones play divergent roles in these different processes. For example, during cervical ripening, important enzymes such as MMPs govern ECM remodeling, via the degradation and turnover of key proteins such as collagen.[8,9,10] As P4 is considered to be the principal suppressor of MMP expression in the endometrium, inhibiting MMP expression and activity may serve as the mechanism for slowing the process of cervical ripening, and suppressing preterm delivery. For uterine contractility, synchronous high-amplitude contractions in cell-cell connections are facilitated by the formation of gap junctions. The formation of these gap junctions is highly dependent on estrogen; estrogen activation, in turn, is induced by a functional progesterone withdrawal at term. Thus, compounds such as P4 operate through distinct and divergent mechanisms of action in the context of cervical ripening and uterine contractility.

Despite the effective use of compounds such as P4 for treating preterm labor and uterine contractile disorders, there are several significant limitations and drawbacks. Current administration techniques often deliver P4 as crystalline progesterone in micronized form, there requiring the inconvenient and less effective routes of vaginal, oral or intramuscular delivery. Further, P4 exhibits some measure of non-specificity for non-progesterone receptors, leading to potentially undesirable side effects.

Trimegestone (TMG) is a member of the 19-norprogesterone derivative family, wherein the core 19-norprogesterone structure originates from the pregnane (19-norpregnane) structure, but possesses one less carbon atom due to a radical methyl removed at C-19. Removal of carbon 19 from steroid hormones, such as testosterone, changes the major hormonal effect from androgenic to prostogenic, with some "19-nor" steroids acting as prodrugs, and other being active in unchanged form. Exemplary members of the 19-norprogesterone family include trimegestone, promegestone, nomegestrol, nomegestrol acetate, demegestone, and nestorone.

A key feature of the 19-norprogesterone family of molecules is high selectivity for the PR. For example, the relative binding affinity (RBA) for TMG-PR interactions is 588, but for TMG-mineralocorticoid receptors (MR), RBA is only 42, thereby demonstrating a high level of separation between RBA for PR compared to other classical steroid hormone receptors.[12,14] This high specificity for PR results in both greater potency (approximately 6 times higher than P4), but also reduces undesirable side-effects via interactions with other steroid hormone receptors.

The potentially effective use of 19-norprogesterone molecules, such as TMG, for suppressing term and pre-term delivery is suggested by several reports demonstrating important interactions with key molecules involved in both cervical ripening and uterine contractility processes. For example, in cultured stromal cells, TMG has been reported to exhibit tighter control of MMP expression, such as MMP-1 and MMP-3, compared to P4 further including suppression of MMP-9+ cell proliferation.[13] Further, the activity of TMG on the rat uterine decidualization and ovulation assays is similar to other progestins, but TMG was the most potent antagonist of estrogenic activity in the uterine endometrium when compared to any of several reference progestins tested.[68]

This potent effect of TMG in the uterus endometrium further suggests new therapeutic avenues, such as treatment of dysmenorrhea. Decidulation has been reported to control eutopic endometrial stromal cell-mediated contractility[69] and application of TMG represents a novel and integral mechanism of regulating the physiological endometrial tissue remodeling process that occurs during menstrual cycles. Similarly, TMG may also be used in early pregnancy to enhance implantation, as a means to supplement endogenous progesterone levels that are low (luteal insufficiency) for the purpose of sustaining pregnancy.

Another key feature of 19-norprogesterone family members, such as TMG, is potential use in more convenient and effective delivery routes. As described, compounds such as P4 have demonstrated effective results when used for treating preterm labor and uterine contractile disorders. However, delivery is often achieved by inconvenient and less effective routes of vaginal, oral or IM administration. By contrast, TMG has shown promise for use in topical applications, such as transdermal contraceptive applications.[15]

Despite these positive results, TMG has yet to be utilized in the prevention and treatment of preterm and term labor and no studies have been published suggesting the potential of TMG as a potential treatment for the prevention and treatment of term and preterm labor. Without being bound by any particular theory, it is suggested that TMG can delay delivery in rats when administered either subcutaneously or topically late in gestation and at lower doses than progesterone (P4), that TMG prevents prostaglandin-induced preterm delivery in guinea pigs and that exogenous TMG and P4 are suitable candidates for treatment of preterm and term labor.

To establish the potential use of TMG as an effective treatment for suppressing pre-term delivery birth, the inventors conducted two studies using animal models. In one study, TMG and P4 were both given topically and parenterally on term delivery in pregnant rats and to assess the ability of TMG to suppress preterm delivery, in pregnant guinea pigs, a model thought to be similar to human endocrine control of pregnancy and parturition.

In the first study, pregnant rats were treated daily beginning on day 20 of gestation with topical P4 (fish oil vehicle) or topical TMG (fish oil vehicle), along with subcutaneous P4 administration (sesame oil vehicle) or subcutaneous TMG administration (benzyl benzoate (BB) and castor oil (CO) vehicle), and vehicle as controls. Various dosage of topical and subcutaneous P4 or TMG administration were applied in order to assess drug efficacy. Delivery times were observed in the animals, wherein time of delivery was measured as the number of hours elapsed after 8 am on day 22 of gestation, and 80 hours being defined as complete block of delivery and time of sacrifice. The inventors discovered that TMG completely blocks term delivery in rats (80 hrs. inhibition) at much lower doses (ca. 30×, 0.5 mg TMG vs. 15 mg P4, $P<0.05$, topically, and ca. 4×, 0.5 mg TMG vs. 2 mg P4, $P<0.05$, subcutaneous) when compared to P4.

In the second study, pregnant guinea pigs were treated with PGE2 (saline vehicle) on days 46 and 47 of gestation to induce preterm delivery[66,67] and sacrificed on day 48. Some animals were given TMG (BB and CO vehicles) beginning on day 44 of gestation until day 47 while also being treated with PGE2 on days 46 and 47, where PGE2 effectively induces preterm delivery. All guinea pigs were sacrificed on day 48. The inventors found that PGE2 induced preterm delivery is inhibited by simultaneous treatment with TMG. None of the guinea pigs treated with TMG and PGE2 delivered, while ⅔ PGE2-only treated animals delivered (all 3 exhibited vaginal bleeding).

Overall, the inventors found that TMG effectively inhibits both term delivery in rats and PGE2-induced preterm delivery in guinea pigs. Both topical and parenteral administration of P4 and TMG are equally efficacious, but TMG is more potent than P4 in delaying delivery in rats. Together, these results demonstrate that TMG is an effective and potent molecule for suppressing preterm and term labor and delivery.

As described herein, the present invention provides a method of extending pregnancy term, including reducing a likelihood of preterm and/or term labor, in a subject by administering a therapeutically effective amount of a composition comprising a progestogen, or a pharmaceutical equivalent, derivative, analog, and/or salt thereof. In another embodiment, the progestogen is 19-norprogesterone or a pharmaceutical equivalent, derivative, analog, and/or salt thereof. In another embodiment, the 19-norprogesterone pharmaceutical equivalent, derivative, analog, and/or salt thereof is trimegestone. In another embodiment, the composition comprises a compound of the formula:

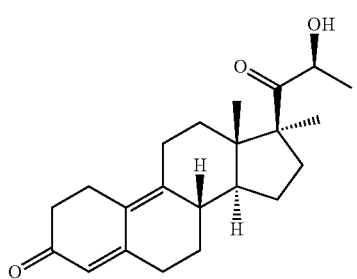

(Formula 1)

or a pharmaceutical equivalent, derivative, analog, and/or salt thereof, and a pharmaceutically acceptable carrier.

In another embodiment, the 19-norprogesterone pharmaceutical equivalent, derivative, analog, and/or salt thereof is promegestone, nomegestrol, nomegestrol acetate, demegestone, nestorone. In another embodiment, the subject is a human. In another embodiment, the subject is a rat. In another embodiment, the subject is a guinea pig. In another embodiment, the composition is administered to the subject topically. In another embodiment, the composition is administered to the subject parenterally. In another embodiment, the effective dosage ranges between 0.05 mg and 100 mg. In another embodiment, the effective dosage ranges between 0.05 mg and 30 mg. In another embodiment, the dosage is 0.05 and 0.50 mg.

In other embodiments, the pregnancy term is at least 20, 21, 22, 23, 24, 25, 26, 27, 28, 29, 30, 31, 32, 33, 34, 35, 36, 37, 38, 39, 40, 41 or 42 weeks. In other embodiments, the pregnancy term is extended by 1, 2, 3, 4, 5, 6, or 7 or more days. In other embodiments, the pregnancy term is extended by 1, 2, 3, 4, 5, 6, 7, 8, 9, 10, 11, 12, 13, 14, 15, 16, 17, 18, 19, 20, 21 or 22 weeks. In some embodiments, preterm labor occurs during weeks 22-37 of pregnancy term. In other embodiments, term labor occurs during weeks 37-42 of pregnancy term. In some embodiments, preterm birth occurs during weeks 22-37 of pregnancy term. In other embodiments, term birth occurs during weeks 37-42 of pregnancy term.

As described herein, the present invention also provides a pharmaceutical composition comprising a therapeutically effective amount of a compound of the formula:

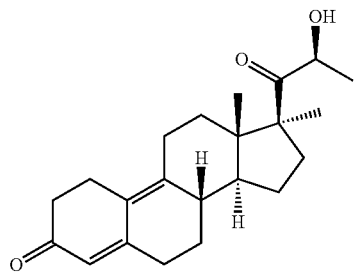

(Formula 1)

or a pharmaceutical equivalent, derivative, analog, and/or salt thereof, and a pharmaceutically acceptable carrier.

In some embodiments, the generic class of "19-nor" steroids, which further includes members of the 19-norprogesterone family, may act as prodrugs, and other being active in unchanged form. Exemplary members of the 19-norprogesterone family include trimegestone, promegestone, nomegestrol, nomegestrol acetate, demegestone, and nestorone. Examples of 19-norprogesterone derivatives and analogs include those described in U.S. Pat. Nos. 3,328,432, 5,223,492, 5,290,771, 6,790,971, 4,263,290, and 4,874,754. Further examples include, 17α-hydroxy 6, 21-dimethyl 3,20-dioxo 19-nor pregna 4,6-diene, 17α-acetoxy 6,21-dimethyl 3,20-dioxo 19-nor pregna 4,6-diene, 17αbutyryloxy 6,21-dimethyl 3,20-dioxo 19-nor pregna 4,6-diene, 17αtetrahydropyranyloxy 6,21-dimethyl 3,20-dioxo 19-nor pregna 4,6-diene, 17αcaproyloxy 6,21-dimethyl 3,20-dioxo 19-nor pregna 4,6-diene, 17α-heptanoyloxy 6,21-dimethyl 3,20-dioxo 19-nor pregna 4,6-diene, and 3,20-dioxo 17α, 21-dimethyl 19-nor pregna 4,9-diene.

Other examples of 19-norprogesterone derivatives and analogs include 11β-N-(2-dimethylaminoethyl)-17β-hydroxy-N-methyl-3-oxo-Δ-estradien-undecanamide, N-butyl-4-(3,17β-dihydroxy-Δestratrien-11β-yl)-N-methyl-benzene octanamide, 3,17β-dihydroxy-N-methyl-N-isopropyl-11β-Δ-estratrien-undecanamide, N-butyl-3,17β-dihydroxy-N-methyl-19-nor-11β-(17α-Δ-pregnatrien-20-yn)-undecanamide, 3,17β-dihydroxy-N-methyl-N-isopropyl-19-nor-11β-17α-Δ-pregnatrien-20-yn)-undecanamide, [[8-(3, 17β-dihydroxy-Δ.sup-estratrien-11β-yl)-octyl]-oxy]-N-methyl-N-isopropyl-acetamide, N-butyl-8-[4-(3,17β-dihydroxy-Δ-estratrien-11β-yl)-phenoxy-N-methyl octanamide, N-butyl-[5-[4-(3,17β-dihydroxy-Δ-estratrien-11β-yl)-phenoxy]-pentoxy]-N- methyl acetamide, 2-[(7-[4-(3,17β-dihydroxy-Δ-estratrien-11β-yl)-phenyl]-6-heptlyl]] oxy]-N-butyl-N-methyl acetamide, 3,17β-dihydroxy-N-(2, 2,3,3,4,4,4-heptafluorobutyl)-N-methyl 1-estratrien-11β-yl undecanamide, 8-[4-(3,17β-dihydroxy-Δ-estratrien-11β-yl)-phenyl]-N-butyl-N-methyl octynamide, β-N-(2-dimethylaminoethyl)-17 β-hydroxy-N-methyl-3-oxo-Δ-estradien-undecanamide, N-butyl-4-(3,17 β-dihydroxy-Δ-estratrien-11 β-yl)-N-methyl-benzene octanamide, 3,17β-dihydroxy-N-methyl-N-isopropyl-11 β-Δ-estratrien-undecanamide, N-butyl-3,17 β-dihydroxy-N-methyl-19-nor-11 β-(17α-Δ-pregnatrien-20-yn)-undecanamide, 3,17 β-dihydroxy-N-methyl-N-isopropyl-19-nor-11β-17α-Δ-pregnatrien-20-yn)-undecanamide, [[8-(3,17 β-dihydroxy-Δ-estratrien-11 β-yl)-octyl]-oxy]-N-methyl-N-isopropyl-acetamide, N-butyl-8-{4-(3,17 β-dihydroxy Δ-estratrien-11β-yl)-phenoxy-N-methyl octanamide, N-butyl-[5-[4-(3,17β-dihydroxy-Δ-estratrien-11β-yl)-phenoxy]-pentoxy]-N-methyl acetamide, 2-[(7-[4-(3,17β-dihydroxy-Δ-estratrien-11β-yl)-pheny]-6-heptyl]-oxy]-N-butyl-N-methyl acetamide, 3,17 β-dihydroxy-N-(2,2,3,3,4,4,4-heptafluorobutyl)-N-methyl-Δ-estratrien-11β-yl]-undecanamide and N-[4-(3,17 β-dihydroxy-Δ-estratrien-11β-yl)-phenyl-N-butyl-N-methyl octynamide.

Other examples of 19-norprogesterone derivatives and analogs include 11β-N-(2-dimethylaminoethyl)-17β-hydroxy-N-methyl-3-oxo-Δ-estradien-undecanamide, 11β-(4-((7-(butylmethylamino)-carbonyl)-heptyl)-oxy-phenyl)-Δ-estratrien-3-ol-17β-yl, butanedioate of 11β-(4-((7-((butylmethylamino)-carbonyl)-heptyl)-oxy)-phenyl)-Δ-estratrien-3-ol-17β-yl and its sodium salt, N-butyl-2-(6-(4-(67-estratrien-3,17β-diol-11β-yl)-phenoxy)-hexyloxy-N-methyl-acetamide, N-butyl-8-(4-(Δ-estratrien-3,17β-diol-11β-yl)-phenoxy)-N-methyl-2-octynamide, N-butyl-2-((5-(4-(Δ-estratrien-3,17β-diol-11β-yl)-phenyl)-pentyl)-thio)-N-methylacetamide, N-butyl-4-(Δ-estratrien-3,17β-diol-11β-yl)-N-methyl-benzenenonamide, N-butyl-2-((5-(4-Δ-estratrien-3,17β-diol-11β-yl)-phenyl)-pentyl)-oxy)-N-methyl-acetamide, and 2-((8-(Δ-19-nor-17α-pregnatrien-3,17β-diol-20-yn-11 β-yl)-octyl)-oxy)-N-methyl N-(1-methylethyl)-acetamide.

Other examples of 19-norprogesterone derivatives and analogs include 7α-{4-[2-(dimethylamino)-ethoxy]-phenyl}-Δ-estratriene-3,17-diol, 7α-{4-[2-dimethylamino)-ethoxy]-phenyl}-17β-hydroxy-Δ-estren-3-one, 7β-{4-[2-(dimethylamino)-ethoxy]-phenyl}-Δ-estratriene-3,17β-diol, 7β-{4-[2-(dimethylamino)-ethoxy]-phenyl}-17β-hydroxy-Δ-estren-3-one; 7α-[4-(dimethylamino)-phenyl]-estratriene-3,17β-diol, 7α-(4-methoxyphenyl)-Δ-estratriene-3,17β-diol-7α-[4-(methylthio)-phenyl]-estren-17β-ol-3-one and 7α-[4-methylthio)-phenyl]-Δ-estratriene-3,17β-diol.

As described herein, the present invention provides a method for inhibiting preterm and/or term birth or preventing preterm birth in a subject in need thereof. In one embodiment, the method includes a composition comprising a steroid hormone and administering a therapeutically effective amount of the composition to the subject to so as to inhibit preterm and/or term birth or prevent preterm and/or term birth. In one embodiment, the steroid hormone is a progestogen, or a pharmaceutical equivalent, analog, derivative or a salt thereof. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof.

As described herein, the present invention also provides a method for delaying cervical ripening or inhibiting cervical ripening in subjects in need thereof. In one embodiment, the method includes providing a composition including a steroid hormone and administering a therapeutically effective amount of the composition to the subject so as to delay cervical ripening or inhibit cervical ripening. In one embodiment, the steroid hormone is a progestogen, or a pharmaceutical equivalent, analog, derivative or a salt thereof. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof. In some embodiments, cervical ripening may be assessed by directly or indirectly measuring the dissolution of connective tissue, according to any number of methods known in the art.

As described herein, the present invention also provides a method for inhibiting myometrial contractility in a subject in need thereof. In one embodiment, the method includes providing a composition including a steroid hormone and administering a therapeutically effective amount of the composition to the subject so as to inhibit myometrial contractility. In one embodiment, the steroid hormone is a progestogen, or a pharmaceutical equivalent, analog, derivative or a salt thereof. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof.

As described herein, the present invention also provides a method for treating uterine contractility disorders or inhibiting uterine contractility disorders in a subject in need thereof. In one embodiment, the method includes providing a composition including a steroid hormone and administering a therapeutically effective amount of the composition to the subject so as to treat uterine contractility disorders or inhibit uterine contractility disorders. In one embodiment, the steroid hormone is a progestogen, or a pharmaceutical equivalent, analog, derivative or a salt thereof. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone is promegestone, nomegestrol, nomegestrol acetate, demegestone, nestorone, or a pharmaceutical equivalent, analog, derivative or a salt thereof. In some embodiments, a uterine contractility disorder may be diagnosed directly or indirectly measuring the muscular contractions associated with the sub-endometrial layer of the myometrium, according to any number of methods known in the art (e.g., endometrial or contractile waves). In another embodiment, the uterine contractility disorder is dysmenorrhea, or other menstrual problems, such as premenstrual symptoms (PMS), discomfort from increased uterine contractions, hypercontractility of the uterus, increased blood flow to uterus, and dysfunctional and/or abnormal uterine bleeding.

In one embodiment, the present invention provides a method of suppressing preterm and/or term delivery in a subject. In one embodiment, the method includes providing a composition including a steroid hormone and administering a therapeutically effective amount of the composition to the subject so as suppress preterm and/or term delivery in the subject. In one embodiment, the steroid hormone is a progestogen, or a pharmaceutical equivalent, analog, derivative or a salt thereof. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof. In some embodiments, preterm delivery is associated with an increase in prostaglandin levels, such as prostaglandin E2.

In other embodiments, the present invention provides a method of treating a disease and/or condition in a subject. In some embodiments, the disease and/or condition is characterized by lower endogenous progesterone levels when compared to healthy subjects. In one embodiment, disease and/or condition is amenorrhea, luteal insufficiency in early pregnancy, infertility, hypercontractility of the uterus, cancer prevention when estogen(s) are used, symptoms associated with hormone replacement therapy (such as hot flashes and osteoporosis), preeclampsia (i.e., pregnancy induced hypertension), and dysfunctional and/or abnormal uterine bleeding.

Since steroid hormones have low solubilities, these hormones may be suspended in or mixed with agents that render the steroid hormones soluble. For instance, suspending or mixing steroid hormones with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, facilitates dissolution. In an embodiment, 19-norprogesterone or pharmaceutical equivalent, derivative, analog, and/or salt thereof, such as trimegestone, may be suspended in or mixed with REPLENS vaginal moisturizer (available from Lil' Drug Store Products, Inc.).

In another embodiment, the steroid hormones may be mixed with carrier molecules such as cyclodextrins to render the steroid hormone soluble. Examples of cyclodextrins include but are not limited to α-cyclodextrin, β-cyclodextrin, γ-cyclodextrin, 2-hydroxypropyl-β-cyclodextrin and methyl-β-cyclodextrin. For example by encapsulating 19-norprogesterone or pharmaceutical equivalent, derivative, analog, and/or salt thereof, such as trimegestone, in cyclodextrins and solubilizing it in any of the agents described above, renders the 19-norprogesterone or pharmaceutical equivalent, derivative, analog, and/or salt thereof soluble and can be used intravenously, topically, parenterally, nasally, subcutaneously, intravascularly, vaginally and/or topically or by other routes of administration.

In some embodiments, steroid hormones such as trimegestone, promegestone, nomegestrol, nomegestrol acetate, demegestone, nestorone and progesterone (P4) or a pharmaceutical equivalent, analog, derivative or a salt thereof, is suspended in or mixed with omega fatty acid, omega-3-fatty acids, fish oil or peppermint oil and may be used topically, parenterally, nasally or by other routes of administration. In one embodiment, administration of 19-norprogesterone or pharmaceutical equivalent, derivative, analog, and/or salt thereof mixed with fish oil or peppermint oil is topical. For example, topical application of 19-norprogesterone or pharmaceutical equivalent, derivative, analog, and/or salt thereof, such as trimegestone, mixed in fish oil can inhibit delivery (such as preterm delivery) in a subject in need thereof.

In another embodiment, trimegestone, promegestone, nomegestrol, nomegestrol acetate, demegestone, nestorone and progesterone (P4) is suspended in or mixed with saline solution (for example isotonic saline solution) to solubilize it and is subsequently administered via numerous routes of administration including but not limited to intravenous, topical, parenteral, nasal, subcutaneous injections, intravascular, vaginal and/or topical or by other routes of administration.

As described herein, the present invention also provides compositions including a steroid hormone and optionally, further includes nifedipine, indomethacin, magnesium sulfate, oxytocin antagonists (for example atosiban), and/or other tocolytics. In one embodiment, steroid hormone and nifedipine may be administered concurrently. In another embodiment, the steroid hormone and nifedipine may be administered sequentially. Similarly, in one embodiment, the steroid hormone and indomethacin may be administered concurrently. In another embodiment, the steroid hormone and indomethacin may be administered sequentially. Similarly, in one embodiment, the steroid hormone and magnesium sulfate may be administered concurrently. In another embodiment, the steroid hormone and magnesium sulfate may be administered sequentially. Additionally, the steroid hormone and oxytocin antagonists (for example atosiban) may be administered concurrently. In another embodiment, the steroid hormone and oxytocin antagonists (for example atosiban) may be administered sequentially. In an additional embodiment, the steroid hormone, nifedipine, indomethacin, magnesium sulfate and/or oxytocin antagonists may be administered concurrently. Alternatively, the steroid hormone, nifedipine, indomethacin, magnesium sulfate and/or oxytocin antagonists may be administered sequentially. In other embodiments, the steroid hormone is administered concurrently or sequentially with tocolytics.

In one embodiment, the steroid hormone is suspended in or mixed with agents that render 19-norprogesterone or pharmaceutical equivalents, derivatives, analogs, and/or salts thereof soluble and is administered concurrently or sequentially with nifedipine, indomethacin, magnesium sulfate, oxytocin antagonists such as atosiban, and/or other tocolytics. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof.

As described herein, the present invention also provides pharmaceutical compositions including a steroid hormone and optionally, further includes nifedipine, indomethacin, magnesium sulfate, oxytocin antagonists, and/or other tocolytics. In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly per os (p.o., by mouth) or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly.

Various methods may be utilized to administer the compositions comprising steroid hormones, including but not limited to aerosol, nasal, oral, subcutaneous, transmucosal, transdermal, parenteral, implantable pump, continuous infusion, topical application, capsules, injections, intradermally, intravenously, intramuscularly, intraperitonealy, rectally, non-vaginally and/or vaginally. In one embodiment of the claimed invention, the steroid hormone is administered topically or subcutaneously. In another embodiment, the steroid hormone is administered vaginally. In another embodiment, the steroid hormone is mixed with or suspended in agents to render it soluble and is applied topically by placing or rubbing on the abdominal surface of pregnant patients. Agents that render the steroid hormones soluble include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution.

In one embodiment of the claimed invention, the steroid hormone is mixed with fish oil or peppermint oil and is applied topically to prevent or inhibit preterm birth and/or delay or inhibit cervical ripening. In one embodiment of the claimed invention, the steroid hormone is mixed with fish oil or peppermint oil and is applied topically to prevent or inhibit preterm birth and/or delay or inhibit uterine contractions. In other embodiments, the steroid hormone is mixed with saline solution (such as isotonic saline solution) and is administered intravenously, topically, nasally or via any other route of administration so as to prevent or inhibit preterm and/or term birth by inhibiting cervical ripening and/or uterine contractility.

In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof.

In various embodiments of the invention, the effective amounts of the steroid hormone is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, 2900-3000 mg/day, 3000-3100 mg/day, 3100-3200 mg/day, 3200-3300 mg/day, 3300-3400 mg/day, 3400-3500 mg/day, 3500-3600 mg/day, 3600-3700 mg/day, 3700-3800 mg/day, 3800-3900 mg/day, 3900-4000 mg/day, 4000-4200 mg/day, 4200-4400 mg/day, 4400-4600 mg/day, 4600-4800 mg/day or 4800-5000 mg/day. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof. In various embodiments, the steroid hormone administered at the aforementioned dosage is trimegestone, promegestone, nomegestrol, nomegestrol acetate, demegestone, nestorone, or a pharmaceutical equivalent, analog, derivative or a salt thereof. In one embodiment, the steroid hormone administered at the aforementioned dosage is trimegestone, promegestone, nomegestrol, nomegestrol acetate, demegestone, nestorone, or a pharmaceutical equivalent, analog, derivative or a salt thereof and is administered daily, biweekly, weekly, every fortnight or monthly. In one embodiment, the steroid hormone administered at the aforementioned dosage is trimegestone, promegestone, nomegestrol, nomegestrol acetate, demegestone, nestorone, or a pharmaceutical equivalent, analog, derivative or a salt thereof and is administered daily.

As described above, in one embodiment of the invention the steroid hormone may be suspended in or mixed with agents that render the steroid hormone soluble. Such agents include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. The effective amount of the agent may be about 0.05-0.1 ml/mg of steroid hormone, 0.1-0.2 ml/mg of steroid hormone, 0.2-0.3 ml/mg of steroid hormone, 0.3-0.4 ml/mg of steroid hormone, 0.4-0.5 ml/mg of steroid hormone, 0.5-0.6 ml/mg of steroid hormone, 0.6-0.7 ml/mg of steroid hormone, 0.7-0.8 ml/mg of steroid hormone, 0.8-0.9 ml/mg of steroid hormone, 0.9-1.0 ml/mg of steroid hormone, 1.0-5.0 ml/mg of steroid hormone, 5.0-10.0 ml/mg of steroid hormone, 10.0-15.0 ml/mg of steroid hormone, 15.0-20.0 ml/mg of steroid hormone, 20.0-25.0 ml/mg of steroid hormone or 25.0-30.0 ml/mg of steroid hormone. In a one embodiment, trimegestone is mixed with fish oil or peppermint oil or with saline solution wherein the aforementioned amounts are the effective amounts of the fish oil or peppermint oil or saline solution. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

In another embodiment of the invention, the steroid hormones may be administered concurrently or sequentially with an effective amount of nifedipine, indomethacin, magnesium sulfate, oxytocin antagonists such as atosiban, and/or other tocolytics. In some embodiments of the invention, the effective amounts of nifedipine, indomethacin, magnesium sulfate, oxytocin antagonists such as atosiban, and/or other tocolytics is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, 2900-3000 mg/day, 3000-3100 mg/day, 3100-3200 mg/day, 3200-3300 mg/day, 3300-3400 mg/day, 3400-3500 mg/day, 3500-3600 mg/day, 3600-3700 mg/day, 3700-3800 mg/day, 3800-3900 mg/day, 3900-4000 mg/day, 4000-4200 mg/day, 4200-4400 mg/day, 4400-4600 mg/day, 4600-4800 mg/day or 4800-5000 mg/day. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

Typical dosages of an effective amount of a steroid hormone, such as trimegestone, promegestone, nomegestrol, nomegestrol acetate, demegestone, nestorone, or a pharmaceutical equivalent, analog, derivative or a salt thereof, can be in the ranges recommended by the manufacturer where known therapeutic compounds are used, and also as indicated to the skilled artisan by the in vitro responses or responses in animal models. The same or similar dosing can be used in accordance with various embodiments of the present invention, or an alternate dosage may be used in connection with alternate embodiments of the invention, with or without oil, nifedipine or indomethacin. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

The subjects treated by the present invention include mammalian subjects, including but not limited to human, monkey, ape, dog, cat, cow, horse, goat, pig, rabbit, mouse and rat.

In one embodiment, the subject is human. In a different embodiment, the human subject is administered a steroid hormone beginning at about the $16^{th}$ week up to the $37^{th}$ week of gestation, beginning at about $18^{th}$ week up to about $22^{nd}$ week of gestation, beginning at about $18^{th}$ week up to about $35^{th}$ week of gestation, beginning at about $18^{th}$ week up to about $37^{th}$ week of gestation, beginning at the time of positive pregnancy until the $37^{th}$ week of gestation or beginning at the time preterm labor is suspected up to when time of delivery is imminent. In an embodiment, the steroid hormone is mixed with or suspended in agents to render the steroid hormones soluble and is applied topically. In some embodiments, the steroid hormone is mixed with fish oil, peppermint oil or with omega fatty acids and is applied topically, for example, by placing or rubbing the 19-norprogesterone or pharmaceutical equivalent, derivative, analog, and/or salt thereof mixed in oil on the abdominal surface of a pregnant woman. In one embodiment, the steroid hormone is mixed with saline solution (such as isotonic saline solution) and is administered intravenously, topically, nasally or via any other route of administration. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

In another embodiment, the human subject is administered a steroid hormone for about 2 to 4 weeks, for about 4 to 6 weeks, for about 6 to 8 weeks, for about 8 to 10 weeks, for about 10 to 12 weeks, for about 12 to 14 weeks, for about 14 to 19 weeks, for about 20 weeks, for about 21 weeks, for about 22 weeks, for about 23 weeks, for about 25 weeks, for about 26 weeks, for about 27 weeks, for about 28 weeks or for about 29 weeks, for about 30 weeks, for about 35 weeks or for about 37 weeks. In an embodiment, the steroid hormone is mixed with or suspended in agents to render the steroid hormones soluble and is applied topically. In one embodiment, the steroid hormone is mixed with fish oil, peppermint oil or with omega fatty acids and is applied topically, for example, by placing or rubbing the 19-norprogesterone or pharmaceutical equivalent, derivative, analog, and/or salt thereof mixed in oil on the abdominal surface of a pregnant woman. In other embodiments, the steroid hormone is mixed with saline solution (such as isotonic saline solution) and is administered intravenously, topically, nasally or via any other route of administration. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

In a further embodiment, the human subject is administered a steroid hormone when the pregnant woman's cervix length is greater than 1.0 cm, or when the cervix length is less than or equal to about 3.0 cm, or when the cervix length is between 1.0 and 8.0 cm. In an embodiment, the steroid hormone is mixed with or suspended in agents to render the steroid hormones soluble and is applied topically. In some embodiments, preterm birth is associated with shorter cervix length. For example, women with cervical lengths at or below the $25^{th}$, $50^{th}$ and $75^{th}$ percentile (i.e., less than 3.0 cm) at 24 weeks may possess increased risk of preterm birth, whereas women with cervical lengths above the $75^{th}$ percentile (i.e., greater than 4.0 cm) may possess decreased risk of preterm birth. In some embodiments, cervical length may be used as a basis for determining a schedule and dosage for administering a steroid hormone. In other embodiments, preterm delivery is associated with an increase in prostaglandin levels, such as prostaglandin E2. In some embodiments, prostaglandin expression levels in the pregnant mother may be used as a basis for determining a schedule and dosage for administering a steroid hormone. In some embodiments, the steroid hormone is a proesetogen. In another embodiment, the progestogen is 19-norprogesterone, or a pharmaceutical equivalent, analog, derivative or a salt thereof. In another embodiment, the 19-norprogesterone pharmaceutical equivalent, derivative, analog, and/or salt thereof is trimegestone, or a pharmaceutical equivalent, analog, derivative or a salt thereof. In another embodiment, the 19-norprogesterone pharmaceutical equivalent, derivative, analog, and/or salt thereof is promegestone, nomegestrol, nomegestrol acetate, demegestone, nestorone, or a pharmaceutical equivalent, analog, derivative or a salt thereof.

In some embodiments, the steroid hormone is mixed with fish oil or with omega fatty acids or with cyclodextrins and is applied topically, for example, by placing or rubbing the 19-norprogesterone or pharmaceutical equivalent, derivative, analog, and/or salt thereof, such as trimegestone, mixed in oil on the abdominal surface of a pregnant woman. In other embodiments, the steroid hormone is mixed with saline solution (such as isotonic saline solution) and is administered intravenously, topically, nasally or via any other route of administration. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

In various embodiments, the steroid hormones are in a soluble form, crystalline form, gel form, tablet form or encapsulated form. In some embodiments, the steroid hormone is a prosteogen. In another embodiment, the progestogen is 19-norprogesterone, or a pharmaceutical equivalent, analog, derivative or a salt thereof. In another embodiment, the 19-norprogesterone pharmaceutical equivalent, analog, derivative or a salt thereof is trimegestone, or a pharmaceutical equivalent, analog, derivative or a salt thereof. In another embodiment, the 19-norprogesterone pharmaceutical equivalent, analog, derivative or a salt thereof is promegestone, nomegestrol, nomegestrol acetate, demegestone, nestorone, or a pharmaceutical equivalent, analog, derivative or a salt thereof.

As described herein, the present invention further provides a kit to treat and/or inhibit preterm and/or term delivery. The kit is an assemblage of materials or components, including at least one of the inventive compositions. Thus, in some embodiments the kit contains a composition including 19-norprogesterone or pharmaceutical equivalent, derivative, analog, and/or salt thereof, such as trimegestone, for topical application, as described above.

In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to apply 19-norprogesterone or pharmaceutical equivalent, derivative, analog, and/or salt thereof, such as trimegestone, topically. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment.

As disclosed herein, the inventors compared and evaluate the inhibitory effects of trimegestone (TMG) and progesterone (P4) (micronized) and have established TMG as a novel treatment for term and preterm labor with significant effects on the delay of delivery. Delay and block of delivery occurs when both P4 and TMG are administered late in gestation in pregnant rat and guinea pig animal models. However, TMG exhibits remarkable drug efficacy, achieving the same inhibition as P4, but at much lower doses. These effects of TMG on processes of cervical ripening and uterine contraction provide a novel approach for treating preterm and/or term labor, along with improved methods of administration. Other diseases and/or conditions may be treated with TMG, such as dysmenorrhea or luteal insufficiency for sustaining pregnancy.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

Trimegestone (TMG), a 19-norpregnane progestin, has been used in clinical trials as a proposed treatment for hormone replacement therapy. TMG binds to the human progesterone receptor with greater affinity (6 times) than progesterone (P4). TMG lacks masculinization or feminization effects of the fetus, making it a suitable candidate for use during pregnancy. The inventors compared and evaluated the inhibitory effects of TMG and P4 (micronized), both given topically and parenterally on term delivery in pregnant rats and to assess the ability of TMG to suppress preterm delivery in pregnant guinea pigs. Additional experiments were performed to confirm sex ratios of delivered animals and to establish sustained fertility.

Example 2

In Vivo Rat Study Design

Pregnant rats, a well-known model for the study of pregnancy in animals, are incredibly sensitive to changes in progesterone levels with preterm, term, or delayed delivery when progesterone levels are altered or when progesterone receptor agonists/antagonists are utilized.[28] The high sensitivity of rat models to changes in progesterone levels demonstrate a decline in progesterone as producing preterm birth while high progesterone levels at term will delay delivery. This allows one to predict with high probability, the effects of progestins, such as TMG, on both term labor and preterm labor.

Timed-pregnant Sprague-Dawley rats (200-250 g) from Charles-River Laboratories (Wilmington, Mass., USA) were delivered to our animal care facilities on day 15 of gestation (day 1 being the day when a sperm plug was observed). The animals were housed separately, with free access to food and water and maintained on a constant 12-hour light-dark cycle. Control pregnant rats were spontaneously delivering on day 22 of gestation. The animals were randomly allocated into groups and sacrificed by carbon dioxide inhalation on day 5 postpartum or on day 25 of gestation in the groups with delayed delivery.

Pregnant rats (N=6 per group) were treated, when not otherwise mentioned, from day 20 of gestation until delivery. Single daily treatments were performed at 8 am and twice a day treatments at 8 am and 8 pm. Treatment began daily on day 20 of gestation with vehicles or: a) Topical P4 at various doses (4-30 mg/day, vehicle (v)=fish oil) or topical TMG (0.5-2 mg/day, v=fish oil; b) Subcutaneous (s.c.) P4 (0.5-4 mg/day, v=sesame oil) or s.c. TMG (0.5-2 mg/day, v=benzyl benzoate(BB) and castor oil (CO), 1:4). Delivery times were observed. Time of delivery=hours after 8 am on day 22 of gestation, 80 hours=complete block of delivery and time of sacrifice.

Example 3

Reagents

Micronized progesterone (used for topical and subcutaneous administration in rats) was purchased from Spectrum Chemical MFG Corp. (Gardena, Calif., USA). PGE2 (used for inducing preterm labor in guinea pigs was purchased from Tocris Bioscience (Ellisville, Mo., USA). Trimegestone purchased from Taizhou Jiakan Chemical Co. Ltd. (Zheijiang, China) and tested for purity by Evestra (San Antonio, Tex.).

Example 4

In Vivo Rat Study: Methods Of Administration

Subcutaneous treatments. All daily injections were by the subcutaneous route (s.c) in fish oil for the P4 treatments and benzyl benzoate (BB, 1 part): castor oil (CO, 4 parts) for the TMG group. P4 and TMG had dose ranges of 0.5 mg-4 mg per day and 0.5 mg-2 mg per day, respectively. Vehicles only are used in the control groups.

Topical treatments. Topical P4 and TMG (in fish oil and benzyl benzoate:castor oil (1:4), respectively) treatments were applied to the shaved back of the rat twice a day For topical treatments of P4 and TMG, dose range from 2 mg-30 mg per day and 0.005 to 0.5 mg per day, respectively.

Example 5

In Vivo Rat Study: Sexing And Fertility

To determine the effects of TMG on progeny sex ratios, pregnant rats (N=9 per group) were treated daily beginning on day 13 of gestation with TMG (in benzyl benzoate+ castor oil, vehicle) or with vehicle only. Because TMG inhibits delivery in pregnant rats, on day 22 of gestation, TMG-treated rats were sacrificed and pups were removed from the uterus and placed with surrogate rat. Pups were then placed with surrogate mother also on day 22 of gestation whose pups were sacrificed.

To determine the effects of TMG on fertility the following procedure was followed. When pups from TMG-treated pregnant rats were of breeding age (5 months) the females were placed with normal (untreated) males for 6 days. Similarly, male pups from TMG-treated rats were placed with normal (untreated) females for 6 days. The ability of the pups to produce offspring was not compromised by the TMG treatments.

Example 6

In Vivo Rat Study: Determining Changes In Delivery Time

Times of delivery of controls and treatment groups were determined as hours after 8 a.m. on day 22 of gestation. An 80-hour delay is classified as complete block of delivery (i.e. 100% inhibition). Delays in delivery less than 80 hours were calculated as less than 100% inhibition. The expulsion of a single pup was noted as delivery. Control groups spontaneously delivered on day 22 of gestation.

Example 7

In Vivo Guinea Pig Study

Pregnant guinea pigs, another model of pregnancy are also utilized as they more closely resemble the endocrine control of human pregnancy with progesterone levels in pregnancy maintained by the placenta as opposed to the ovaries, which is observed in pregnant rats.

Pregnant Hartley guinea pigs arrived at our facilities at 31-35 days gestation and housed in pairs, with free access to food and water and also maintained on a constant 12-hour light-dark cycle. The animals were euthanized with a combination of xylazine (Gemini; Burns Veterinary Supply Inc, Rockville Center, N.Y.) and ketamine HCL (Ketaset; Fort Dodge Laboratories Inc, Fort Dodge, Iowa). All procedures were approved by the Animal Care and Use Committee of the St. Joseph's Hospital and Medical Center in Phoenix, Ariz.

Pregnant guinea pigs (N=4-6 per group) were allocated into 4 groups (Vehicle (v) only, TMG only, PGE2 only, PGE2+TMG). PGE2 administration (3 mg/day s.c, v=saline) began daily on day 46 to day 47 of gestation. TMG administration (4 mg/day s.c v=BB:CO) began daily on day 44 until day 47 of gestation. All guinea pigs were sacrificed on day 48.

Example 8

Statistical Analyses

The Student's t test was used to compare the treatment groups with its specific control groups to determine the differences in delivery times. A 2-tailed probability value of $P<0.05$ was considered statistically significant.

Example 9

Effects Of Treatments On Time Of Delivery In Pregnant Rats

As shown in FIGS. 1-4, the inventors discovered that TMG completely blocks term delivery in rats (80 hrs. inhibition) at much lower doses (ca. 30×, 0.5 mg TMG vs. 15 mg P4, $P<0.05$, topically, and ca. 4×, 0.5 mg TMG vs. 2 mg P4, $P<0.05$, s.c) when compared to P4.

Figure 5:
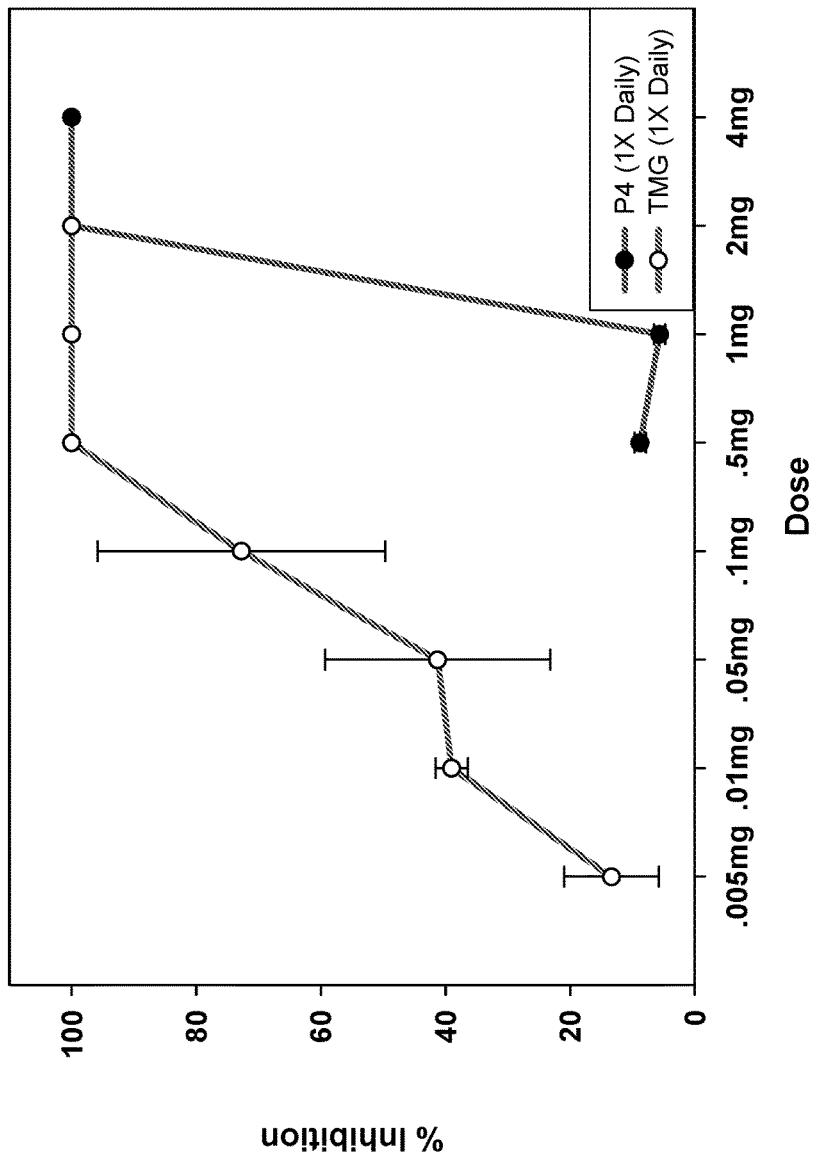
FIG. 5: depicts, in accordance with an embodiment herein, comparison of dose/response effects of subcutaneous (s.c.) treatments between trimegestone (TMG) and progesterone (P4) on delay of delivery in pregnant rats. Much lower doses of TMG are required for complete block (>80 hours beyond normal delivery on day 22) compared to P4 block of delivery. Percent inhibition of delivery is shown where 80 hour delay (day 25) denotes 100 percent inhibition. Complete inhibition can be seen with s.c TMG at much lower doses than s.c P4 (0.5 mg vs. 2 mg).
Figure 6:
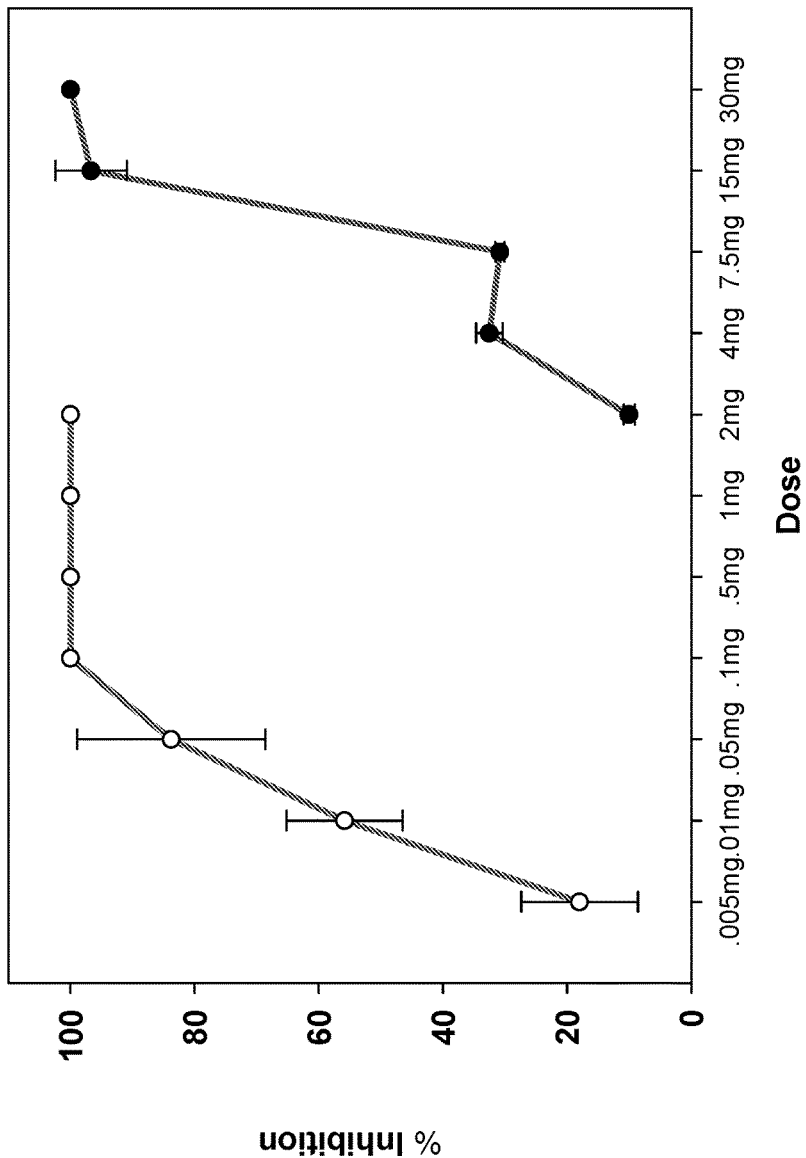
FIG. 6 depicts, in accordance with an embodiment herein, comparison of dose/response effects of topical progesterone (P4) or trimegestone (TMG) in delay of delivery in pregnant rats. Much lower doses of TMG are required for complete block (>80 hours beyond normal delivery on day 22) compared to P4 block of delivery. Percent inhibition of delivery is shown at 80 hour delay (day 25) denoted as 100 percent inhibition. Complete inhibition can be seen with topical TMG at much lower doses than topical P4 (0.1 mg vs. 15 mg).
Figure 7:
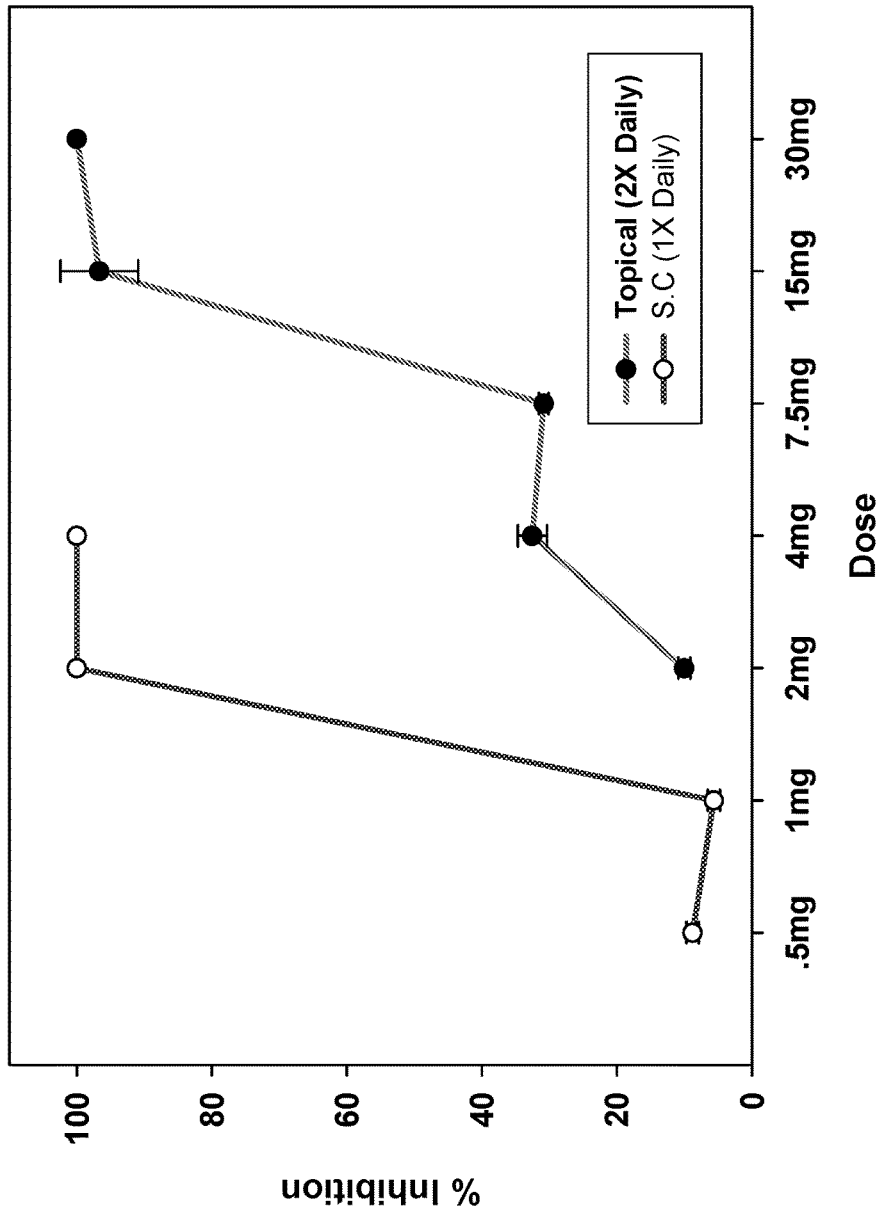
FIG. 7 depicts, in accordance with an embodiment herein, dose/response effects topical and subcutaneous (s.c) progesterone (P4) on delay of delivery in rats. Dose response curves shows that lower daily doses are required for complete block of delivery when P4 is administered s.c. when given on day 20 of gestation. Complete block of delivery is seen at 80 hour delay (day 25) and denoted by 100 percent inhibition. Topical group received treatments twice a day while subcutaneous group received a single daily treatment. Subcutaneous administration of P4 required lower doses than topical to completely block delivery (2 mg vs. 15 mg).
Figure 8:
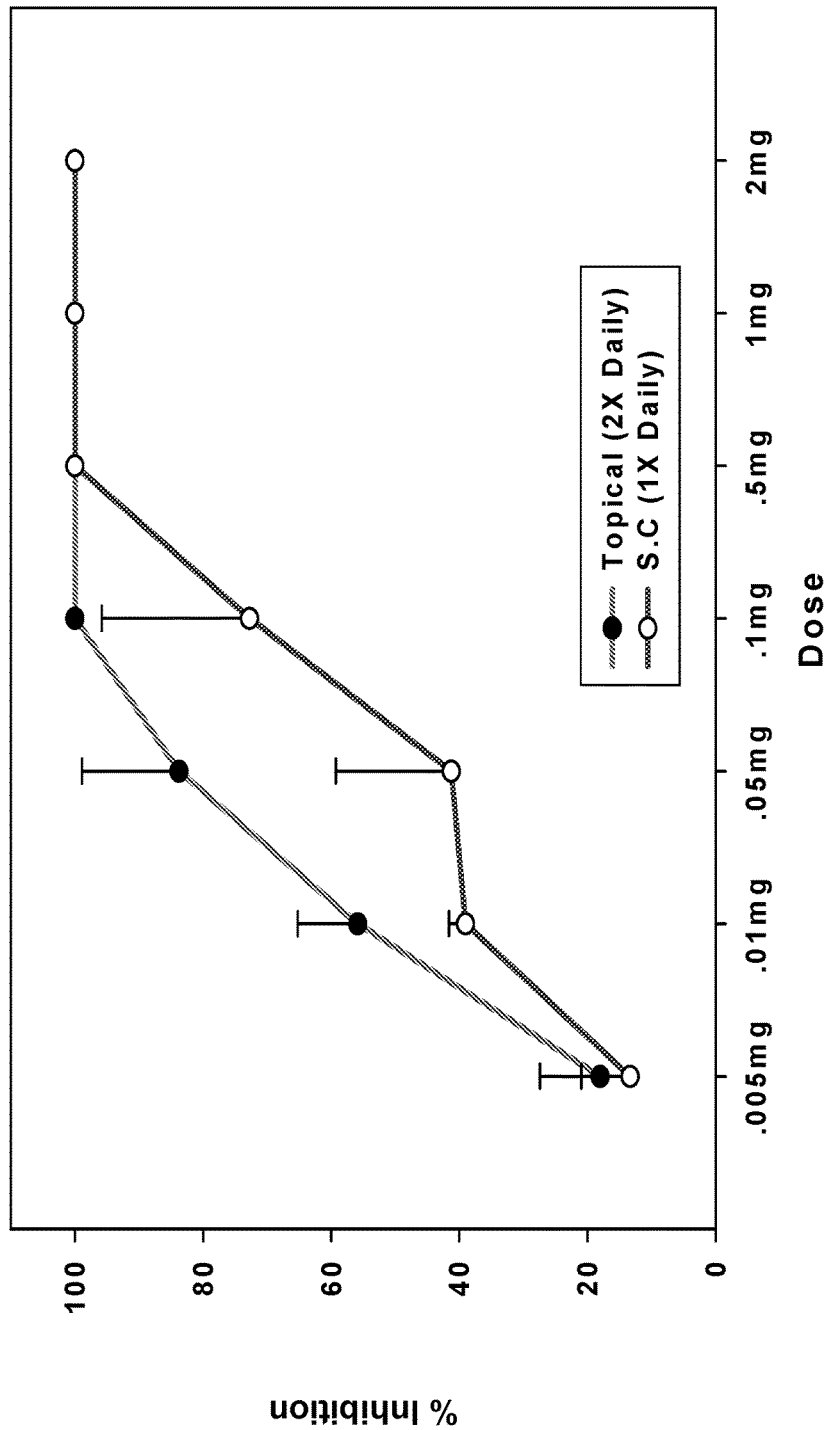
FIG. 8 depicts, in accordance with an embodiment herein, effects of trimegestone (TMG) between topical or subcutaneously (s.c) on delay of delivery in rats. Note that a lower dose is required for complete block of delivery when TMG is administered topically. Complete block of delivery is seen at 80 hour delay (day 25) and denoted by 100 percent inhibition. Topical group received treatments twice a day while subcutaneous group received a single daily treatment. Each point represents total amount of TMG given per day. Topical administration of TMG required slightly lower doses than subcutaneous to completely block delivery, possible because TMG was given twice daily due to a shorter half-life.

FIG. 5 further summarizes the results of the different treatment groups on time of delivery and shows multiple doses of subcutaneous trimegestone (TMG) and progesterone (P4). Complete block of delivery was observed at 0.5 mg/day TMG and 2 mg/day P4. FIG. 6 shows the results of time of delivery after topical treatment with TMG or P4. Complete block of delivery was seen at 0.1 mg/day TMG and 15 mg/day P4. FIG. 7 establishes a dose response for topical and subcutaneous P4. 2 mg of P4 necessary for complete block of delivery, subcutaneously and 15 mg P4 needed for topical treatments. FIG. 8 details topical and subcutaneous treatments of TMG where 0.1 mg/day blocks delivery, topically, and 0.5 mg/day blocks delivery subcutaneously. These results clearly show that TMG is a highly potent and effective molecule for inhibiting term and preterm labor, even when compared to leading compound P4.

Example 10

Effects of Treatments of TMG on Rat Pup Sex

Figure 9:
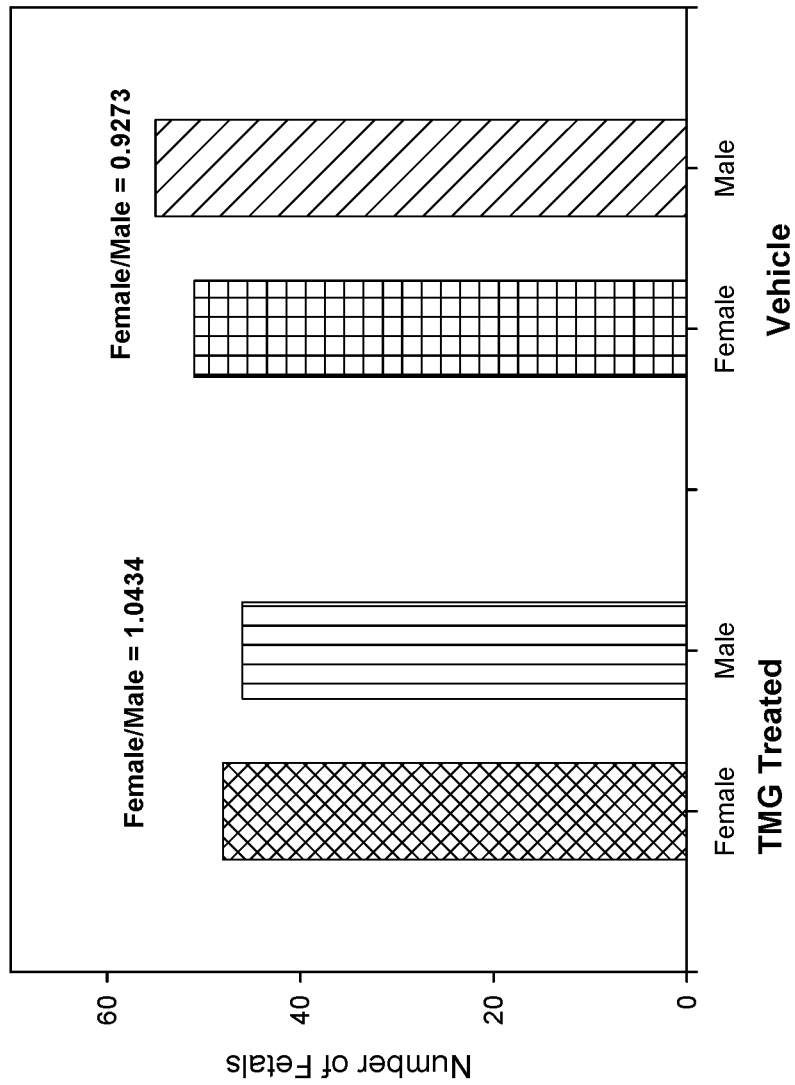
FIG. 9 depicts, in accordance with an embodiment herein, sex of pups of rats treated with either of trimegestone (TMG) or vehicle beginning on day 13 of gestation until day 22. TMG treated and controls demonstrated non-significant differences between the number of females to males. For TMG Group (N=9), TMG was administered from day 13 to day 21, when mother rats were sacrificed and pups were taken from uterus and placed with surrogate mother rat that had just delivered. For vehicle control (N=9), BB:CO (1:4) mixture was administered subcutaneously in 0.2 ml volume from day 13 to day 21 of gestation. As shown, no change is sex ratio is observed.

As described, the sex of the pups was evaluated 21 days post-partum by examining external genitalia as well as distance between rectum and genitalia. TMG demonstrated no significant difference in the ratio of male to female pups when compared to control groups (FIG. 9).

Example 11

Effects of TMG Treatment on Fertility

Similarly fertility of the offspring (both male and females) of TMG-treated rats was not compromised by the treatment. Females (n=6) from TMG-treated rats became pregnant following breeding with normal (untreated) males and similarly males (n=6) from TMG-treated rats mated successfully with normal (untreated) females to produce offspring

Example 12

Effects of Treatments of PGE2, TMG on Guinea Pig Pregnancy

Figure 11:
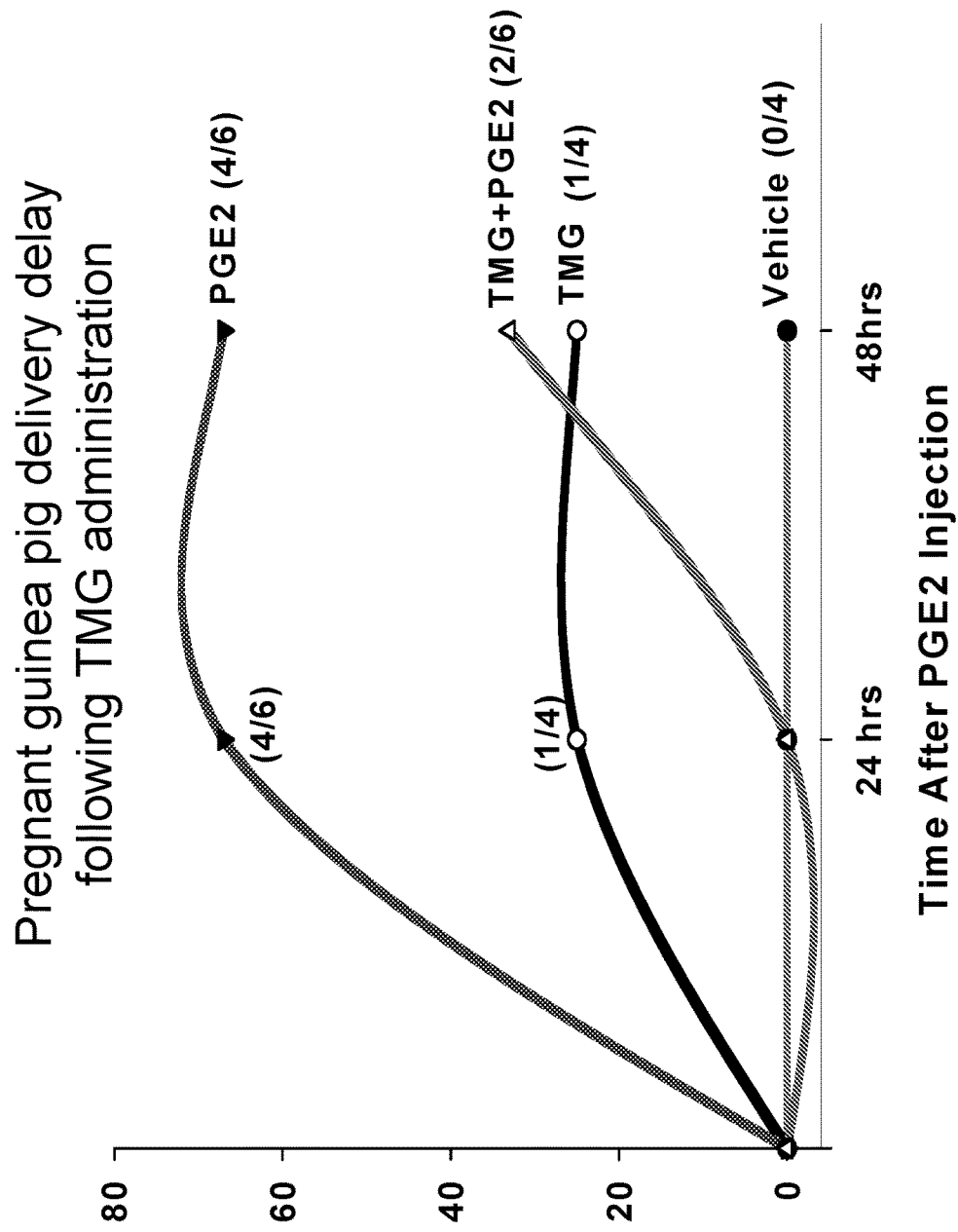
FIG. 11 depicts, in accordance with an embodiment herein, effects of prostaglandin E2 (PGE2), or trimegestone (TMG) and its combination on delay of delivery in Guinea Pig. Preterm delivery rates of guinea pigs treated with vehicle, TMG and PGE2 and TMG plus PGE2. Vehicle only group was treated with 0.5 ml s.c of a mixture of benzyl benzoate and castor oil (1:4) on days 44-47 and 0/4 guinea pigs delivered. TMG only group was treated with 4 mg/day s.c on days 44-47 and 1/4 guinea pigs delivered. PGE2 only group was treated with 3 mg/day in saline vehicle on days 46, 47 and 4/6 guinea pigs delivered. PGE2 plus TMG group was treated with TMG from days 44-47 and PGE2 on days 46-47 and 2/6 guinea pigs delivered.

TMG effectively inhibited preterm delivery stimulated by administration of PGE2 in the pregnant guinea pig when administered mid-gestation. (FIG. 11) The inventors found that in guinea pigs, PGE2 effectively induces preterm delivery, and this is inhibited by simultaneous treatment with TMG. None of the guinea pigs treated with TMG and PGE2 delivered, while ⅔ PGE2-only treated animals delivered (all 3 exhibited vaginal bleeding).

Example 13

TMG Effectively Inhibits Term and Preterm Labor

As disclosed herein, it was found that TMG effectively inhibits both term delivery in rats and PGE2-induced preterm delivery in guinea pigs. Both topical and parenteral administration of P4 and TMG are equally efficacious, but TMG is more potent than P4 in delaying delivery in rats. Topical TMG is be a successful and satisfactory treatment option for preterm and/or term labor.

This study shows that TMG can be useful in the delay of delivery at preterm and at term. TMG has never been described for the prevention and treatment of preterm labor and these results indicate a tremendous utility for use in the clinical setting. Both P4 and TMG were shown to work topically and subcutaneously, but TMG required much lower doses when compared to P4. In the rat studies, TMG proved to be effective at delaying delivery even when administered late in gestation (day 20). This effect of TMG is consistent with other results that show P4 inhibition of birth even after the cervix is already soft, thereby emphasizing a specific action of TMG on uterine contractility to prevent birth. The guinea pig studies utilizing PGE2 to stimulate preterm birth demonstrated the lower delivery rates of animals treated with both TMG and PGE2 versus PGE2 alone. As a model of preterm birth, PGE2 induction studies in the pregnant guinea pig provides results consistent with another specific action directed at inhibiting the process of cervical ripening. Thus, TMG exhibits properties of a highly efficacious inhibitor of preterm and term labor, possessing specific actions directed at key steps involving both cervical ripening and uterine contraction.

Figure 10:
FIG. 10 depicts, in accordance with an embodiment herein, photograph of male (right) and female (left) fetuses on day 22 of gestation after treatment with TMG beginning on day 13 of pregnancy. Note that the distance between the external genitalia and the anus is greater distance in males.

Dose response curves for the complete block of delivery in pregnant rats were established in this study for both P4 and TMG when administered either topically or subcutaneously. FIGS. 5 and 6 show that much lower doses of TMG are required to block delivery when given either topically or subcutaneously most likely due to its ability to bind more effectively to the progesterone receptor than P4. Moreover, TMG also demonstrated no masculinizing or feminizing effects on the fetuses of treated animals (FIG. 10) or on subsequent fertility of both female and male offspring of TMG-treated rats. These results show improved methods of administration, along with minimized risk of undesirable side effects.

Both topical and subcutaneous administration of P4 and TMG demonstrated prolonged delay of delivery with subcutaneous treatment groups requiring less dosage except in the topical vs. subcutaneous TMG treatment experiment. Topical TMG worked more effectively at delaying delivery than subcutaneous administration. This result may be explained by TMG's half-life of 17 hours and the twice daily administration of topical TMG versus the once daily administration of subcutaneous TMG. Without being bound by any particular theory, the levels of TMG in the topical group may have remained higher throughout the course of the treatments.

These results present TMG as a novel treatment for preterm and term labor with the TMG exhibits remarkable drug efficacy, the effects of TMG on processes of cervical ripening and uterine contraction provide a novel approach for extending pregnancy term, including reducing a likelihood of preterm and/or term labor, along with improved methods of administration.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources and composition of progestogens, including 19-norprogesterone derivatives such as trimegestone, further including pharmaceutical compositions, preparation methods, dosages, administration methods, and/or other diseases and conditions and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

1. Goldenberg R, Culhane J, Jams J, Romero R. Epidemiology and causes of preterm birth. Lancet 2008; 371: 75-84.
2. Steer P. The epidemiology of preterm labour. BJOG 2005; 112 Suppl 1:1-3.
3. Martin J A, Hamilton B E, Sutton P D, Ventura S J, Menacker F, Kirmeyer S, Mathews T J. Births: Final Data for 2006. Natl Vital Stat Rep 2009; 57:1-104.
4. Berkowitz G S, Papiernik E. Epidemiology of preterm birth. Epidemiol Rev 1993; 15(2):414-43.
5. Behrman R, Butler A. Preterm Birth: Causes, Consequences, and Prevention. Washington, D.C: The National Academies Press; 2007: 398-429.
6. Uldbjerg N, Ekman G, Malmström A, Olsson K, Ulmsten U. Ripening of the human uterine cervix related to changes in collagen, glycosaminoglycans, and collagenolytic activity. Am J Obstet Gynecol 1983; 147:662-6.
7. Rechberger T, Uldbjerg N, Oxlund H. Connective tissue changes in the cervix during normal pregnancy and pregnancy complicated by cervical incompetence. Obstet Gynecol 1988; 71(4):563-7.
8. Chwalisz K, Benson M, Scholz P, Daum J, Beier H M, Hegele-Hartung C. Cervical ripening with the cytokines IL-8, IL-1β1-beta and TNFα in guinea-pigs. Hum Reprod 1994; 9:2173-81.
9. Junqueira L C, Zugaib M, Montes G S, Toledo O M, Krisztan R M, Shigihara K M. Morphologic and histochemical evidence for the occurrence of collagenolysis and for the role of neutrophilic polymorphonuclear leukocytes during cervical dilation. Am J Obstet Gynecol 1980; 138:273-81.
10. Osmers R, W Rath, B C Adelmann-Grill, C Fittkow, M Kuloczik, M Szeverényi, H Tschesche, W Kuhn: Origin of cervical collagenase during parturition. Am J Obstet Gynecol 1992; 166(5): 1455-60.
11. Robin-Jagerschmidt C, Wurtz J-M, Guillot B, Gofflo D, Benhamou B, Vergezac A, Ossart C, Moras D and Philibert D (2000) Residues in the ligand binding domain that confer progestin or glucocorticoid specificity and modulate the receptor transactivation capacity. Mol Endocrinol 14, 1028-1037.
12. Winneker R C, Bitran D, Zhang Z. The preclinical biology of a new potent and selective progestin: trimegestone. Steroids. 2003 Nov:68(10-13):915-920
13. Wahab M, Taylor A H, Pringle J H, Thompson J, Al-Azzawi F. Trimegestone differentially modulates the expression of matrix metalloproteinase in the endometrial stromal cell. 2006; 12:157-167.
14. Zhang Z, Lundeen S G, Zhu Y, et al. In vitro characterization of trimegestone: a new potent and selective progestin. Steroids. 2000 October-November:65(10-11):637-43
15. Maillard-Salin D G, Bécourt P, Couarraze G. Physical evaluation of a new patch made of a progestomimetic in a silicone matrix. 2000; 199(1):29-38.
16. Maul H, Shi L, Marx S G, Garfield R E, Saade G R. Local application of platelet-activating factor induces cervical ripening accompanied by infiltration of polymorphonuclear leukocytes in rats. Am J Obstet Gynecol. 2002; 187:829-33.
17. Facchinetti F, Paganelli S, Comitini G, Dante G, Volpe A. Cervical length changes during preterm cervical ripening: effects of 17-alpha-hydroxyprogesterone caproate. Am J Obstet Gynecol 2007; 196:453.e1-4; discussion 421.
18. DeFranco E A, O'Brien J M, Adair C D, Lewis D F et al. Vaginal progesterone is associated with a decrease in risk for early preterm birth and improved neonatal outcome in women with a short cervix: a secondary analysis from a randomized, double-blind, placebo-controlled trial. Ultrasound Obstet Gynecol 2007; 30:697-705.
19. Fittkow C T, Shi S Q, Bytautiene E, Olson G, Saade G R, Garfield R E. Changes in light-induced fluorescence of cervical collagen in guinea pigs during gestation and after sodium nitroprusside treatment. J Perinat Med 2001; 29:535-43.
20. Johnson J W, Austin K L, Jones G S, Davis G H, King T M. Efficacy of 17alpha-hydroxyprogesterone caproate in the prevention of premature labor. N Engl J Med 1975; 293:675-80.
21. Keirse M J. Progestogen administration in pregnancy may prevent preterm delivery. Br J Obstet Gynaecol 1990; 97:149-54.
22. Meis P J, Klebanoff M, Thom E et al. Prevention of recurrent preterm delivery by 17 alpha-hydroxyprogesterone caproate. N Engl J Med 2003; 348:2379-85.
23. Da Fonseca E B, Bittar R E, Carvalho M H, Zugaib M. Prophylactic administration of progesterone by vaginal suppository to reduce the incidence of spontaneous preterm birth in women at increased risk: a randomized placebo-controlled double-blind study. Am J Obstet Gynecol 2003; 188:419-24.
24. Keirse M J. Progesterone and preterm: seventy years of "déjà vu" or "still to be seen"? Birth 2004; 31:230-5.
25. O'Brien J M, Adair C D, Lewis D F et al. Progesterone vaginal gel for the reduction of recurrent preterm birth:

25. primary results from a randomized, double-blind, placebo-controlled trial. Ultrasound Obstet Gynecol 2007; 30:687-96.
26. Fonseca E B, Celik E, Parra M, Singh M, Nicolaides K H. Progesterone and the risk of preterm birth among women with a short cervix. N Engl J Med 2007; 357: 462-9.
27. Durnwald C P, Lynch C D, Walker H, Jams J D. The effect of treatment with 17 alpha-hydroxyprogesterone caproate on changes in cervical length over time. Am J Obstet Gynecol 2009; 201:410.e1-5.
28. Garfield R E, Gasc J M, Baulieu E E. Effects of the antiprogesterone RU 486 on preterm birth in the rat. Am J Obstet Gynecol 1987; 157:1281-5.
29. Fittkow C T, Maul H, Olson G, Martin E, MacKay L B, Saade G R, Garfield R E. Light-induced fluorescence of the human cervix decreases after prostaglandin application for induction of labor at term. Eur J Obstet Gynecol Reprod Biol 2005; 123:62-6.
30. Shi L, Shi S Q, Saade G R, Chwalisz K, Garfield R E. Changes in cervical resistance and collagen fluorescence during gestation in rats. J Perinat Med 1999; 27:188-94.
31. O'Brien J M, Defranco E A, Adair C D, Lewis D F, Hall D R, How H, Bsharat M, Creasy G W. Effect of progesterone on cervical shortening in women at risk for preterm birth: secondary analysis from a multinational, randomized, double-blind, placebo-controlled trial. Ultrasound Obstet Gynecol 2009; 34:653-9.
32. Society for Maternal Fetal Medicine Publications Committee. ACOG Committee Opinion number 419 October 2008 (replaces no. 291, November 2003). Use of progesterone to reduce preterm birth. Obstet Gynecol 2008; 112:963-5.
33. Garfield R E, Puri C P, Csapo A I. Endocrine, structural, and functional changes in the uterus during premature labor. Am J Obstet Gynecol 1982; 142:21-7.
34. Pepe G J, Rothchild I. A comparative study of serum progesterone levels in pregnancy and in various types of pseudopregnancy in the rat. Endocrinology 1974; 95:275-9.
35. Peyron R, Aubény E, Targosz V, Silvestre L, Renault M, Elkik F, Leclerc P, Ulmann A, Baulieu E E. Early termination of pregnancy with mifepristone (RU 486) and the orally active prostaglandin misoprostol. N Engl J Med 1993; 328:1509-13.
36. Chwalisz K. The use of progesterone antagonists for cervical ripening and as an adjunct to labour and delivery. Hum Reprod 1994; 9 Suppl 1:131-61.
37. Zakar T, Hertelendy F. Progesterone withdrawal: key to parturition. Am J Obstet Gynecol 2007; 196:289-96.
38. Yellon S M, Ebner C A, Elovitz M A. Medroxyprogesterone acetate modulates remodeling, immune cell census, and nerve fibers in the cervix of a mouse model for inflammation-induced preterm birth. Reprod Sci. 2009; 16:257-64.
39. Ruddock N K, Shi S Q, Jain S, Moore G, Hankins G D, Romero R, Garfield R E. Progesterone, but not 17-alpha-hydroxyprogesterone caproate, inhibits human myometrial contractions. Am J Obstet Gynecol 2008; 199:391e1-7.
40. Stjernholm-Vladic Y, Wang H, Stygar D, Ekman G, Sahlin L. Differential regulation of the progesterone receptor A and B in the human uterine cervix at parturition. Gynecol Endocrinol 2004; 18(1):41-6.
41. Mesiano S. Myometrial progesterone responsiveness and the control of human parturition. J Soc Gynecol Investig 2004; 11:193-202.
42. Cicinelli E. Intravaginal oestrogen and progestin administration: advantages and disadvantages. Best Pract Res Clin Obstet Gynaecol 2008; 22(2):391-405.
43. De Ziegler D, Bulletti C, De Monstier B et al. The first pass uterine effect. Ann N Ann N Y Acad SciY Acad Sci 1997; 828:291-299.
44. Cicinelli E, Cignarelli M, Sabatelli S, Romano F, Schonauer L M, Padovano R, Einer-Jensen N. Plasma concentrations of progesterone are higher in the uterine artery than in the radial artery after vaginal administration of micronized progesterone in an oil-based solution to postmenopausal women. Fertil Steril 1998; 69:471-3.
45. Levine H, Watson N. Comparison of the pharmacokinetics of crinone 8% administered vaginally versus Prometrium administered orally in postmenopausal women (3). Fertil Steril 2000; 73:516-21.
46. Richardson J L, Illum L. The vaginal route of peptide and protein drug delivery. Adv Drug Deliv Rev 1992; 8:341-366.
47. Cicinelli E, Di Naro E, De Ziegler D et al. Placement of the vaginal 17b-estradiol tablets in the inner or outer one third of the vagina affects the preferential delivery of 17b-estradiol towards the uterus or peri-urethral areas, thereby modifying efficacy and endometrial safety. Am J Obstet Gynecol 2003; 189:55-58.
48. Schindler A E, Campagnoli C, Druckmann R, Huber J, Pasqualini J R, Schweppe K W, Thijssen J H. Classification and pharmacology of progestins. Maturitas 2008; 61:171-80.
49. Garfield R E, Kannan M S, Daniel E E. Gap junction formation in myometrium: control by estrogens, progesterone, and prostaglandins. Am J Physiol 1980; 238:C81-9.
50. Garfield R E, Saade G, Buhimschi C, Buhimschi I, Shi L, Shi S Q, Chwalisz K. Control and assessment of the uterus and cervix during pregnancy and labour. Hum Reprod Update 1998; 4:673-95.
51. Shi S Q, Maner W L, Mackay L B, Garfield R E. Identification of term and preterm labor in rats using artificial neural networks on uterine electromyography signals. Am J Obstet Gynecol 2008; 198:235.e1-4.
52. Sexton D J, O'Reilly M W, Friel A M, Morrison J J. Functional effects of 17alpha-hydroxyprogesterone caproate (17P) on human myometrial contractility in vitro. Reprod Biol Endocrinol 2004; 2:80.
53. PeriStats [online database]. White Plains, N.Y.: March of Dimes; 2006. Available from: http://www.marchofdimes.com/peristats/[accessed on April 2006].
54. Blumenfeld Y J, Lyell D J, Prematurity prevention: the role of acute tocolysis. Curr Opin Obstet Gynecol. 2009; 21:136-41.
55. Higby K, Xenakis E M, Pauerstein C J, Do tocolytic agents stop preterm labor? A critical and comprehensive review of efficacy and safety. Am J Obstet Gynecol. 1993; 168:1247-59.
56. Hassan S S, Romero r, Vidyadhari D, et al. Vaginal progesterone reduces the rate of preterm birth in women with a sonographic short cervix: a multicenter, randomized, double-blind, placebo-controlled trial. Ultrasound Obstet Gynecol. 2011 July:38(1):18-31.
57. Ross D, Godfree V, Cooper A, et al. Endometrial effects of three doses of trimegestone, a new orally active progestogen, on the postmenopausal endometrium. Maturitas. 1997 September:28(1):83-8.
58. Koninckx P R, Spielmann D. A comparative 2-year study of the effects of sequential regimensof 1 mg 17beta-estradiol and trimegestone with a regimen containing estradiol valerate and norethisterone on the bleeding profile and endometrial safety in postmenopausal women. Gynecol Endocrinol. 2005 August:21(2):82-9.
59. Grubb G, Spielmann D, Pickar J, et al. Clinical experience with trimegestone as a new progestin in HRT. Steroids. 2003 November:68(10-13):921-6.
60. Meuwissen J H, Beijers-De Bie L, Vihtamaki T, et al. A 1-year comparison of the efficacy and clinical tolerance in postmenopausal women of two hormone replacement therapies containing estradiol in combination with either norgestrel or trimegestone. Gynecol Endocrinol. 2001 October:15(5):349-58.
61. Sitruk-Ware R. New progestagens for contraceptive use. Hum Reprod Update. 2006 March-April: 12(2):169-78.
62. Sitruk-Ware R, Nath A. The use of newer progestins for contraception. Contraception.
2010 November:82(5):410-7.
63. Sitruk-Ware R, Bossemeyer R, Bouchard P. Preclinical and clinical properties of trimegestone: a potent and selective progestin. Gynecol Endocrinol. 2007 June:23(6):310-9.
64. Philibert D, Bouchoux F, Degryse M, et al. The pharmacological profile of a novel norpregnance progestin (trimegestone). Gynecol Endocrinol. 1999 October:13(5): 316-26.
65. Bouchoux F, Cerede E and Philibert D (1995) Measurement of the relative binding affinity of RU27987 to recombinant human steroid receptors: progestogen, glucocorticoid, androgen and oestrogen determination of the binding parameters of RU27987 and progesterone for the recombinant human progesterone receptor. 1995; 93/5353/PH data on file at Roussel-Uclaf.
66. Ylva Vladic-Stjemholm, et al. Prostaglandin treatment is associated with a withdrawal of progesterone and androgen at the receptor level in the uterine cervix. Reprod. Biol Endocrinol 2009, 7:116.
67. Raybur W F Prostaglandin E2 gel for cervical ripening and induction of labor; a critical analysis.
68. Tsuno A, Nasu K, Yuge A, Matsumoto H, Nishida M, Narahara H. Decidualization attenuates the contractility of eutopic and ectopic endometrial stromal cells: implications for hormone therapy of endometriosis. J Clin Endocrinol Metab. 2009 July; 94(7):2516-23. Epub 2009 Apr. 7.
69. Lundeen S G, Zhang Z, Zhu Y, Carver J M, Winneker R C. Rat uterine complement C3 expression as a model for progesterone receptor modulators: characterization of the new progestin trimegestone. J Steroid Biochem Mol Biol. 2001 August; 78(2):137-43.

The invention claimed is:

1. A method of extending pregnancy term in a subject in need thereof, comprising:
providing a quantity of a composition comprising trimegestone or a salt thereof and one or more solubilizing factors selected from sesame oil, corn oil, olive oil, coconut oil, flaxseed oil, argan oil, and castor oil; and
administering the quantity of the composition to the subject in need thereof, wherein the composition is administered through transdermal delivery; wherein the effective dosage range of the trimegestone or salt thereof is between 0.05 mg and 100 mg; and wherein the pregnancy term is extended by an additional one day to 22 weeks.

2. The method of claim 1, further comprising administering of one or more compounds selected from the group consisting of: nifedipine, indomethacin, magnesium sulfate, oxytocin antagonists, and tocolytics.

3. The method of claim 2, wherein the one or more compounds is administered after administering the quantity of the composition comprising the trimegestone and one or more solubilizing factors.

4. The method of claim 1, wherein the composition is administered at least twice daily.

5. The method of claim 1, wherein the composition is administered to the subject in the range of: 0.1-0.5 mg, 0.5-1 mg, 1-5 mg, 5-10 mg, 10-15 mg, 15-20 mg, or 20-100 mg.

6. The method of claim 1, wherein the pregnancy term is at least 22 weeks.

7. The method of claim 1, wherein the pregnancy term is at least 37 weeks.

8. The method of claim 1, wherein the composition comprises trimegestone and castor oil.

9. The method of claim 1, wherein the composition comprises trimegestone and argan oil.

10. The method of claim 1, wherein the composition comprises trimegestone and flaxseed oil.

11. The method of claim 1, wherein the composition comprises trimegestone and coconut oil.

12. The method of claim 1, wherein the composition comprises trimegestone and olive oil.

13. The method of claim 1, wherein the composition comprises trimegestone and corn oil.

14. The method of claim 1, wherein the composition comprises trimegestone and sesame oil.

* * * * *